(12) United States Patent
Toth et al.

(10) Patent No.: US 9,027,408 B2
(45) Date of Patent: May 12, 2015

(54) ELASTOMERIC PARTICLE HAVING AN ELECTRICALLY CONDUCTING SURFACE, A PRESSURE SENSOR COMPRISING SAID PARTICLES, A METHOD FOR PRODUCING SAID SENSOR AND A SENSOR SYSTEM COMPRISING SAID SENSORS

(75) Inventors: Landy Toth, Newtown, PA (US); Johan Wallen, Linkoping (SE)

(73) Assignee: Swelling Solutions, Inc., Minneapolis, MN (US)

( * ) Notice: Subject to any disclaimer, the term of this patent is extended or adjusted under 35 U.S.C. 154(b) by 638 days.

(21) Appl. No.: 12/524,312

(22) PCT Filed: Jan. 24, 2007

(86) PCT No.: PCT/EP2007/000567
§ 371 (c)(1),
(2), (4) Date: Jan. 22, 2010

(87) PCT Pub. No.: WO2008/089787
PCT Pub. Date: Jul. 31, 2008

(65) Prior Publication Data
US 2010/0130889 A1 May 27, 2010

(51) Int. Cl.
*G01L 9/02* (2006.01)
*H01C 7/10* (2006.01)
(Continued)

(52) U.S. Cl.
CPC .................. *H01B 1/22* (2013.01); *G01L 1/205* (2013.01); *H01C 10/106* (2013.01); *H01C 10/12* (2013.01)

(58) Field of Classification Search
CPC ................................. H01B 1/22; H01C 10/12
USPC .......................................... 338/22 R; 601/48
See application file for complete search history.

(56) References Cited

U.S. PATENT DOCUMENTS 2,951,817 A 9/1960 Myers
3,629,774 A 12/1971 Crites
(Continued)

FOREIGN PATENT DOCUMENTS

DE 4031012 4/1992
EP 0210002 1/1987
(Continued)

OTHER PUBLICATIONS

Mallory GO et al., Electroless plating: Fundamentals and Applications; American Electroplaters and Surface Finishers Society, Florida, 1990; Chapters 1, 7, 10, 12, 14-19.
(Continued)

*Primary Examiner* — Devin Henson
(74) *Attorney, Agent, or Firm* — Mueting, Raasch & Gebhardt, P.A.

(57) ABSTRACT

An elastomeric particle (1, 1', 1") comprises a non-conducting elastomeric body (2) having an electrically conducting surface (4a, 4b, 6). Pressure sensor elements (20, 20', 20''; 30, 30', 30'', 30''') comprising such elastomeric particles are disclosed, as well as sensor clusters (50''', 50''', 50$^{IV}$, 50$^{V}$, 50$^{VI}$, 50$^{VII}$, 70) comprising such sensor elements. There is also disclosed a pressure sensor element (40, 40', 40'', 40''', 40$^{IV}$, 40$^{V}$, 40$^{VI}$, 40$^{VII}$), comprising a resistive element (44, 44', 44'') providing a conduction path, a first electrode (42a, 42a-1, 42a-2, 42a-3, 42a-4, 42a-5, 42a-6), connected to the resistive element, a second electrode (42b, 42b'), which in a quiescent state is spaced from said first electrode, wherein the second electrode, when the pressure sensor element is subjected to a pressure, is arranged to contact said first electrode or said resistive element. Systems comprising such sensor elements and sensor clusters are disclosed, as well as methods of their fabrication.

6 Claims, 13 Drawing Sheets

(51) Int. Cl.

| | |
|---|---|
| H01C 7/13 | (2006.01) |
| A61H 1/00 | (2006.01) |
| H01B 1/22 | (2006.01) |
| G01L 1/20 | (2006.01) |
| H01C 10/10 | (2006.01) |
| H01C 10/12 | (2006.01) |

(56) References Cited

U.S. PATENT DOCUMENTS

| | | |
|---|---|---|
| 3,826,249 A | 7/1974 | Lee et al. |
| 4,054,540 A | 10/1977 | Michalchik |
| 4,292,261 A | 9/1981 | Kotani |
| 4,996,511 A | 2/1991 | Ohkawa |
| 5,132,658 A | 7/1992 | Dauenhauer |
| 5,175,214 A | 12/1992 | Takaya |
| 5,240,644 A | 8/1993 | Barry, Jr. |
| 5,296,837 A | 3/1994 | Yaniger |
| 5,302,936 A | 4/1994 | Yaniger |
| 5,416,462 A | 5/1995 | Demarmels |
| 5,452,878 A | 9/1995 | Gravesen et al. |
| 5,453,653 A | 9/1995 | Zumeris |
| 5,575,762 A | 11/1996 | Peeler et al. |
| 5,583,303 A * | 12/1996 | Franz ................ 73/862.046 |
| 5,626,556 A | 5/1997 | Tobler et al. |
| 5,948,990 A | 9/1999 | Hashida |
| 5,997,465 A | 12/1999 | Savage |
| 6,010,471 A | 1/2000 | Ben-Noon |
| 6,025,202 A | 2/2000 | Natan |
| 6,076,013 A | 6/2000 | Brennan et al. |
| 6,121,870 A | 9/2000 | Ariga |
| 6,123,681 A | 9/2000 | Brown, III |
| 6,198,204 B1 | 3/2001 | Pottenger |
| 6,242,264 B1 | 6/2001 | Natan |
| 6,291,568 B1 | 9/2001 | Lussey |
| 6,329,617 B1 * | 12/2001 | Burgess ................ 200/61.43 |
| 6,388,556 B1 | 5/2002 | Imai |
| 6,458,327 B1 | 10/2002 | Vossmeyer |
| 6,494,852 B1 | 12/2002 | Barak |
| 6,592,945 B2 | 7/2003 | Suzuki |
| 6,613,350 B1 | 9/2003 | Zhang et al. |
| 6,620,116 B2 | 9/2003 | Lewis |
| 6,624,886 B2 | 9/2003 | Natan |
| 6,714,019 B2 | 3/2004 | Kirbayashi et al. |
| 6,749,556 B2 | 6/2004 | Banik |
| 6,765,335 B2 | 7/2004 | Wischnewskiy |
| 6,862,942 B2 * | 3/2005 | Kawahata ............. 73/862.046 |
| 6,899,829 B2 | 5/2005 | Shelnut |
| 6,914,100 B2 | 7/2005 | Urano et al. |
| 7,044,924 B1 | 5/2006 | Roth et al. |
| 7,056,297 B2 | 6/2006 | Dohno et al. |
| 7,074,200 B1 | 7/2006 | Lewis |
| 7,074,849 B2 | 7/2006 | Nakayoshi |
| 7,080,562 B2 | 7/2006 | Knowles et al. |
| 7,214,847 B1 | 5/2007 | Flick |
| 7,257,051 B2 | 8/2007 | Thomenius et al. |
| 7,327,637 B2 | 2/2008 | Chambers et al. |
| 7,360,430 B2 * | 4/2008 | Rezgui ......................... 73/719 |
| 7,491,185 B2 | 2/2009 | Couvillon, Jr. |
| 7,548,015 B2 | 6/2009 | Benslimane et al. |
| 7,569,974 B2 | 8/2009 | D'Almeida et al. |
| 7,573,064 B2 | 8/2009 | Benslimane et al. |
| 7,618,384 B2 | 11/2009 | Nardi et al. |
| 7,637,879 B2 | 12/2009 | Barak et al. |
| 7,732,999 B2 | 6/2010 | Clausen et al. |
| 7,785,905 B2 | 8/2010 | Benslimane |
| 7,868,221 B2 | 1/2011 | Munch-Fals et al. |
| 7,880,371 B2 | 2/2011 | Benslimane et al. |
| 7,895,728 B2 | 3/2011 | Benslimane et al. |
| 7,976,924 B2 | 7/2011 | Stanford, Jr. et al. |
| 7,992,217 B2 | 8/2011 | Hyde et al. |
| 8,079,969 B2 | 12/2011 | Rousso et al. |
| 8,083,644 B2 | 12/2011 | Purdy et al. |
| 8,100,841 B2 | 1/2012 | Rousso |
| 8,100,842 B2 | 1/2012 | Rousso |
| 8,105,252 B2 | 1/2012 | Rousso |
| 8,257,289 B2 | 9/2012 | Vess |
| 8,394,042 B1 | 3/2013 | Mirza |
| 8,578,939 B1 | 11/2013 | Kimani Mwangi et al. |
| 2002/0125890 A1 | 9/2002 | Kiribayashi |
| 2002/0173735 A1 | 11/2002 | Lewis |
| 2003/0125781 A1 * | 7/2003 | Dohno et al. ................ 607/75 |
| 2003/0178221 A1 * | 9/2003 | Chiu et al. ............... 174/117 F |
| 2004/0073146 A1 | 4/2004 | Weintraub et al. |
| 2004/0167375 A1 | 8/2004 | Couvillon |
| 2005/0043657 A1 | 2/2005 | Couvillon |
| 2005/0064204 A1 | 3/2005 | Lalli |
| 2005/0081640 A1 | 4/2005 | Knowles |
| 2006/0058456 A1 | 3/2006 | Parekh |
| 2006/0074362 A1 | 4/2006 | Rousso et al. |
| 2008/0255494 A1 | 10/2008 | Rousso et al. |
| 2009/0064476 A1 | 3/2009 | Cross et al. |
| 2009/0118651 A1 | 5/2009 | Rousso et al. |
| 2009/0234265 A1 | 9/2009 | Reid, Jr. et al. |
| 2010/0010404 A1 | 1/2010 | Nardi et al. |
| 2010/0010406 A1 | 1/2010 | Nardi et al. |
| 2010/0204803 A1 | 8/2010 | Tozzi et al. |
| 2011/0009795 A1 | 1/2011 | Graham et al. |
| 2011/0066093 A1 | 3/2011 | Vess |
| 2011/0119812 A1 | 5/2011 | Genz et al. |
| 2011/0156530 A1 | 6/2011 | Yamamoto et al. |
| 2011/0162200 A1 | 7/2011 | Benslimane et al. |
| 2011/0196269 A1 | 8/2011 | Arkans |
| 2013/0345610 A1 | 12/2013 | Larson et al. |

FOREIGN PATENT DOCUMENTS

| | | |
|---|---|---|
| EP | 0210002 A1 | 1/1987 |
| EP | 0475752 B1 | 3/1992 |
| EP | 1 533 678 A1 | 11/2003 |
| EP | 1324403 | 5/2005 |
| EP | 1596794 B1 | 11/2005 |
| EP | 1 645 254 A1 | 4/2006 |
| JP | 2003-344201 | 12/2003 |
| JP | 4961482 B2 | 6/2012 |
| WO | 9405985 | 3/1994 |
| WO | 2004093763 | 11/2004 |
| WO | 2006/071690 | 7/2006 |
| WO | 2007005036 | 1/2007 |
| WO | 2008/089787 A1 | 7/2008 |
| WO | WO 2009/083049 A1 | 7/2009 |
| WO | WO 2009/114676 A1 | 9/2009 |
| WO | 2011/022305 A2 | 2/2011 |
| WO | WO 2013/033669 A2 | 3/2013 |

OTHER PUBLICATIONS

Elvin et al., "Synthesis and properties of crosslinked recombinant pro-resilin," *Nature*, Oct. 2005; 437(7061): 999-1002.

Gregory et al., "Conductive Textiles," *Synthetic Metals*, Jan. 1989; 28(1-2):823-835.

Hansen et al., "Integration of conducting polymer network in non-conductive polymer substrates," *Synthetic Metals*, Nov. 2006; 156(18-20):1203-1207.

International Search Report mailed Jul. 4, 2007, in The Netherlands for International Patent Application No. PCT/EP2007/000567, filed Jan. 24, 2007.

International Preliminary Report on Patentability issued Jul. 28, 2009, in Switzerland for International Patent Application No. PCT/EP2007/000567, filed Jan. 24, 2007.

Mar., "Polygons of resistors and convergent series," *American Journal of Physics*, Oct. 1993; 61(10): 900.

van der Schuur et al., "Polyurethane elastomers with amide chain extenders of uniform length," *Polymer*, Feb. 2006; 47(4): 1091-1100.

Written Opinion mailed Jul. 24, 2009, in Germany for International Patent Application No. PCT/EP2007/000567, filed Jan. 24, 2007.

Yaniger, "Force Sensing Resistors: A Review of the Technology," Conference Proceedings Article, Apr. 16, 1991: 666-668.

* cited by examiner

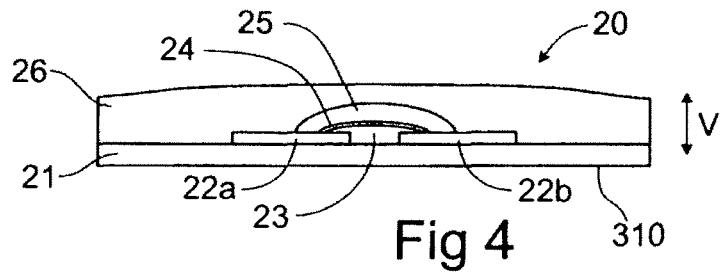
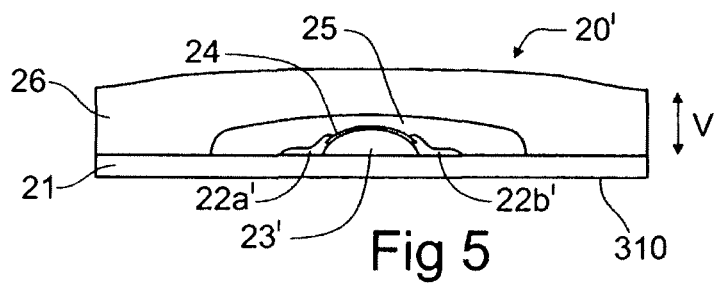
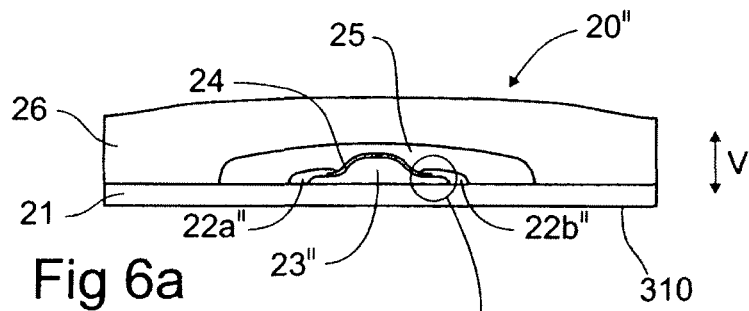
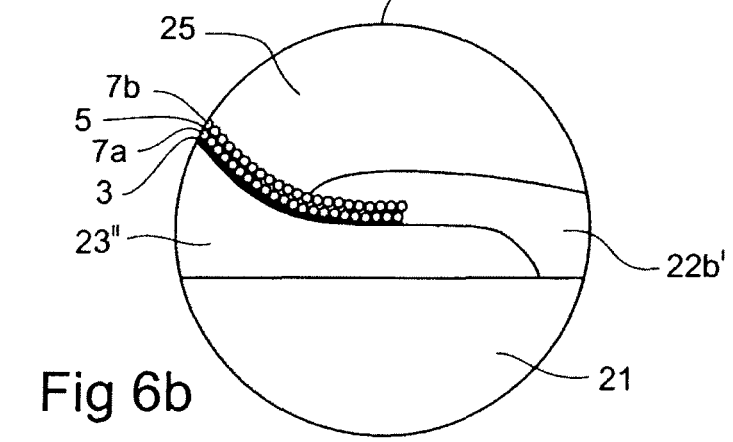

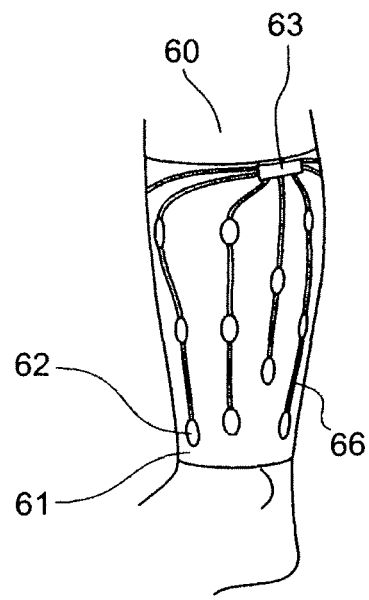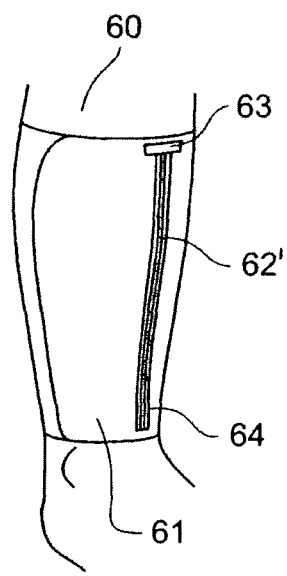
Fig 34   Fig 35
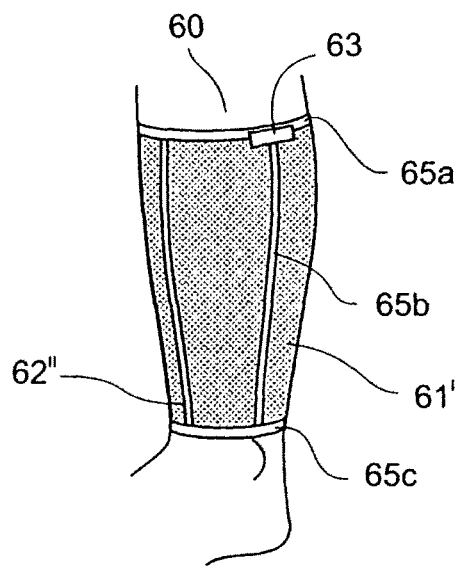
Fig 36

ELASTOMERIC PARTICLE HAVING AN ELECTRICALLY CONDUCTING SURFACE, A PRESSURE SENSOR COMPRISING SAID PARTICLES, A METHOD FOR PRODUCING SAID SENSOR AND A SENSOR SYSTEM COMPRISING SAID SENSORS

BACKGROUND OF THE INVENTION

The present disclosure relates to pressure sensors and systems comprising such sensors. In particular, the present disclosure is directed towards sensors and sensor systems that may be used for measuring pressure on a body part.

Hence, the present disclosure relates to particles that may form part of sensor elements, sensor systems, clusters of sensor elements and devices for measuring pressure on a body part.

There are many applications in which it may be desirable to measure pressure on a body part. As a non-limiting example, it may be desirable to measure pressure on a body part in connection with compression treatment of the body part. Compression therapies may be used for treatment and/or prophylaxis of a number of conditions, including, but not limited to, Deep Vein Thrombosis (DVT), vascular disorders, circulatory disorders, edemas, heart conditions (treated by counterpulsation), lymphedema, burns, injuries, and embolisms.

Some devices for compression treatment are known in the art, e.g., from US 2004/0073146 AI, US 2004/0073146 AI, US 2002/0173735 AI, U.S. Pat. No. 6,494,852 B1, U.S. Pat. No. 5,997,465, U.S. Pat. No. 6,123,681, U.S. Pat. No. 6,198, 204 B1, EP 1 324 403 AI, US 2004/0167375 AI, WO 2004/093763 AI and US 2005/0043657 AI.

Presently available systems for measuring pressure on a body part, however, suffer from a number of drawbacks. Major issues with existing measurement systems have been identified in the areas of mismatched mechanical properties (body/device impedance mismatches and resulting interface stress modification), sensitivity (often too high), quiescent impedance (often nearly infinite), nonlinearity, poor repeatability (cycle to cycle and insertion to insertion), creep, hysteresis, and sensitivity to curvature, temperature-pressure-humidity, etc.

Generally existing sensors have excellent precision (which is good) and perform well at high pressures in planar, mechanically isolated spaces between well characterized surfaces. Such spaces and surfaces are not available in the case of devices for measuring pressure on a body part.

U.S. Pat. No. 2,951,817 discloses a variable resistance material, comprising a body of elastomeric polyvinyl chloride with a granular filler selected from a group consisting of precipitated manganese dioxide and microphone carbon granules.

U.S. Pat. No. 3,629,774 discloses a progressively collapsible variable resistance element, comprising an elastic cellular structure of, e.g., elastomer foam. Examples given include silicone rubber, natural rubber, latex and polyurethane rubber. The element further comprises a conducting coating provided on the inside of the cells in the structure. Examples of coating materials are carbon (graphitized, partially graphitized, carbon black), silver, gold, copper, tungsten, aluminum, and other metals.

U.S. Pat. No. 4,292,261 discloses a pressure sensitive conductor and method of manufacturing the same. The conductor comprises an isolating elastomer having electrically conductive magnetic particles dispersed therein.

U.S. Pat. No. 6,388,556 B1 discloses a film pressure sensitive resistor and pressure sensitive sensor. The film comprises a binder, spherical elastomeric particles and conductive particles, such as carbon black. Examples of conductive particles comprise graphite, carbon black, indium-doped tin oxide and the like. Examples of elastic organic fillers comprise silicone polymer, acrylic polymer, styrene polymer, urethane polymer and the like. Examples of spherical elastomeric particles comprise nylon particles. The binder may be a silicone rubber, polyurethane resin, epoxy resin, phenol resin or polyester resin.

U.S. Pat. No. 6,291,568 B1 discloses a polymer composition comprising an electrically conductive filler material selected from a group consisting of powder-form metallic elements and alloys, electrically conductive oxides of such elements or alloys and mixtures thereof, mixed with a non-conductive elastomer.

The above described sensors are of a conductive elastomer type, and constitute composites of an elastomeric matrix and a conductive particle filler. When such composites are used in practice, strain related damage occurs easily, and as such, creep, hysteresis, and electrical aging are all increased significantly. At such high loading levels so as to induce finite quiescent impedance, the viscoelastic properties of the composite degrade dramatically and their usefulness as "pressure sensors" is greatly diminished.

U.S. Pat. No. 6,388,556 B1 discloses, as prior art for the invention patented therein, a variable area type pressure sensor, wherein a conduction path between first and second coplanar electrodes is variable in response to a pressure applied on the sensor. It is recognized that this type of sensor does not provide a smooth resistance-load curve.

Such sensors do not provide the desired accuracy needed in measuring pressure on a body part.

Hence, there is a need for improvements in sensors for measuring pressure on a body part.

SUMMARY OF THE INVENTION

It is thus a general object of the present disclosure to provide a sensor or sensors that overcome, or at least alleviate, the problems associated with prior art sensors.

It is an object to provide a sensor or sensors that are sufficiently accurate and have sufficiently high precision for measuring pressures at an interface.

It is also an object to provide a sensor or sensors that are suitable for measuring pressure, in particular contact pressure, applied to a human or animal body.

It is also an object to provide a sensor or sensors that can be produced at a sufficiently low cost.

The invention is defined by the appended independent claims. Embodiments are set forth in the dependent claims, and in the following description and drawings.

According to a first aspect, there is provided an elastomeric particle, comprising a non-conducting elastomeric body having an electrically conducting surface. The conducting surface is organized such that the overall mechanical properties of the particle are governed by the elastomeric body of the particle, while the electrical properties are governed by the conducting surface.

Such an elastomeric particle may be suitable for use in a pressure sensor element, i.e., it may be sufficiently small, and suitable for inclusion of a plurality of such elastomeric particles in a matrix to provide a composite material, whose conduction properties are variable in response to mechanical deformation of the sensor element.

Such particles may thus be utilized to form a composite material having pressure sensitive electrical properties and reduced creep, hysteresis and/or electrical aging, as compared with prior art composite materials.

According to a second aspect, reduced creep, hysteresis and/or electrical aging, as compared with prior art composite materials there is provided a pressure sensor element, comprising a plurality of particles having at least conducting surfaces, said particles being arranged as at least one particle layer on a non-conducting elastomeric portion.

Such a pressure sensor element may be used to form in situ a composite of particles and a matrix material.

The particles may be elastomeric particles as set forth above. Alternatively, the particles may be non-elastomeric.

According to a third aspect, there is provided composite material comprising particles having a first modulus of elasticity and electrically conductive surface; and an elastomeric matrix material having a second modulus of elasticity, wherein said first modulus of elasticity is different from said second modulus of elasticity, and wherein the particles are elastomeric.

Such a composite material may be used to form a pressure sensor element. In particular, such a soft conducting particle composite may be used to better manage damage, electrical impedance and strain sensitivity within the composites by improving stresses at interfaces between conducting particles and matrix and within the matrix. Furthermore, hysteresis and strain related damage within composite are reduced, and finite quiescent impedance can be set during fabrication via alignment, volumetric ratios of constituents and fabrication conditions (solvents, compression, temperature profile during curing, etc). Also, pressure sensitivity may be determined primarily by the equivalent hardnesses and the structure of the sensor built from the composite, in terms of geometry, field orientation, electrode placement, etc.

According to a fourth aspect, there is provided a printable compound for forming the composite material as described above, the compound comprising said particles and a composition or compositions for forming the matrix material.

Such a printable compound may be applied in a desired pattern for forming portions of the composite material according to the third aspect.

According to a fifth aspect, there is provided a pressure sensor element comprising a composite material as described above.

According to a sixth aspect, there is provided a sensor system comprising at least one sensor element as described above, and means for receiving a sensor signal from said sensor element.

According to a seventh aspect, there is provided a pressure sensor element, comprising a resistive element providing a conduction path, a first electrode, connected to the resistive element, a second electrode, which in a quiescent state is spaced from said first electrode, wherein the second electrode, when the pressure sensor element is subjected to a pressure, is arranged to contact said first electrode or said resistive element.

Such a sensor element may have improved mechanical response and aging characteristics, immunity to EMI, and the ability to be used for inline calibration of compression systems. Such a pressure sensor element may be used individually, or in combination with sensors or sensor clusters according to the other aspects, to provide an accurate pressure value, and/or for calibration purposes.

According to an eight aspect, there is provided a sensor system comprising at least one pressure sensor element as described above and means for receiving a sensor signal from said sensor element.

According to a ninth aspect, there is provided a sensor cluster, comprising at least three sensor elements wherein the sensor cluster comprises at least one sensor element or group of sensor elements, which is connected in parallel with another sensor element, or group of sensor elements, and at least one sensor element or group of sensor elements, which is connected in series with another sensor element, or group of sensor elements. The cluster may be an organized collection of miniature sensory elements and electrical traces.

Such a sensor cluster may be used to provide an average pressure value over an area, based on a plurality of sensor elements, without having to handle values from each individual sensor element. The sensor cluster also provides a means of measuring pressure with thinner sensors than an equivalently sized sensor of the prior art. It also provides a means of measuring characteristics of the applied pressure over the entire cluster in a fast, simple and economical way. The cluster also decreases sensitivity to curvature, thereby improving sensor performance on non-planar or uneven surfaces.

Such a sensor cluster may also comprise sensor elements forming a circuit, a reduced equivalent circuit of which substantially comprises a polygon network element.

A polygon network element of order N is a network consisting of N+I separate nodes, one of which may be termed "main node" and N of which may be termed "minor nodes", wherein each minor node is connected to the main node by a circuit element, and is connected to two other minor nodes by circuit elements.

By "substantially a polygon network element", is understood that circuit elements may be missing or added from the perfect polygon network element, however, not to such an extent as to seriously impair the effect of the polygon network element. As non-limiting examples, there may be one or a few circuit elements may be missing as compared to the perfect polygon network element, or there may be one or a few circuit elements added as compared to the perfect polygon network element.

According to a tenth aspect, there is provided a sensor system comprising at least one sensor cluster as described above and means for receiving a sensor signal from said sensor element.

According to an eleventh aspect, there is provided a sensor system, comprising at least one first pressure sensor element according to either or both of the second or fifth aspects and at least one second pressure sensor element according to the seventh aspect.

Such a sensor system may be used for measuring pressure on a body part.

According to an eleventh aspect, there is provided a device for measuring pressure on a body part, comprising a sensor system as described above.

According to a twelfth aspect, there is provided a method for producing a sensor element, comprising providing a substrate, dispensing, in a first desired pattern on the substrate, a primer, and dispensing, at least in said desired pattern, particles having a conducting surface.

According to a thirteenth aspect, there is provided a method for producing a sensor element, comprising providing a substrate, dispensing, in a desired pattern on the substrate, a compound according to the fourth aspect, and allowing said compound to set, whereby said composite material is formed.

According to a fourteenth aspect, there is provided a method for producing a sensor element, comprising providing a first substrate, providing a resistive element on the substrate by a first patterning operation, providing a first electrode on the substrate by a second patterning operation, providing a spacer element on the substrate, and providing a second substrate comprising a second electrode, such that said spacer element is between the first electrode and the second electrode.

BRIEF DESCRIPTION OF THE DRAWINGS

FIG. 4 is a schematic cross-sectional view of a sensor element according to a first type of embodiment of the present disclosure.

FIG. 5 is a schematic cross-sectional view of a sensor element according to the first type of embodiment of the present disclosure.

FIGS. 6a and 6b are schematic cross-sectional views of a sensor element according to the first type of embodiment of the present disclosure.

FIGS. 34-36 schematically illustrate devices for measuring pressure on a body part.

DETAILED DESCRIPTION OF THE PREFERRED EMBODIMENTS

Figure 1A:
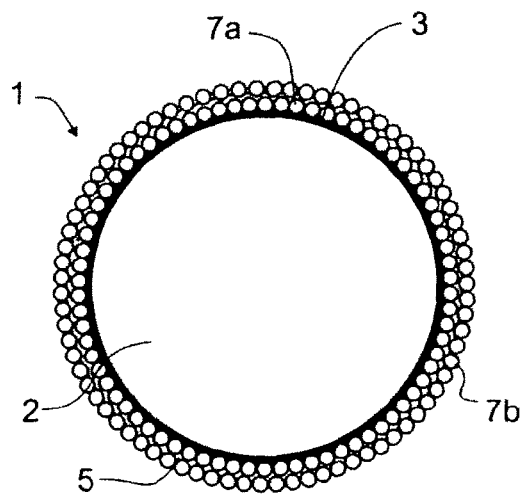
FIGS. 1a-1b are schematic cross-sectional views of different embodiments of a particle according the present disclosure.
Figure 1B:
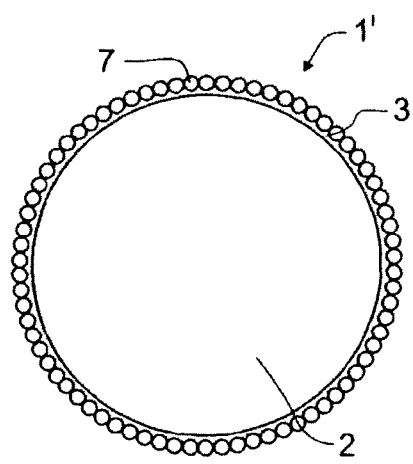
Figure 2A:
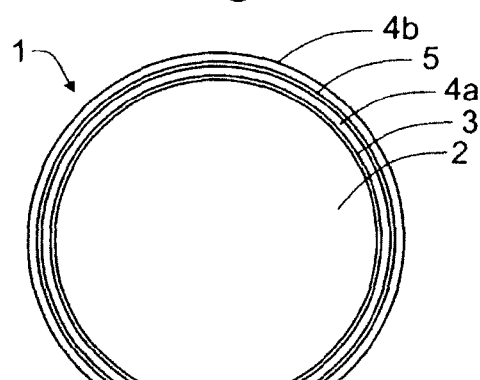
FIGS. 2a-2b are schematic cross-sectional views of further embodiments of a particle according the present disclosure.
Figure 2B:
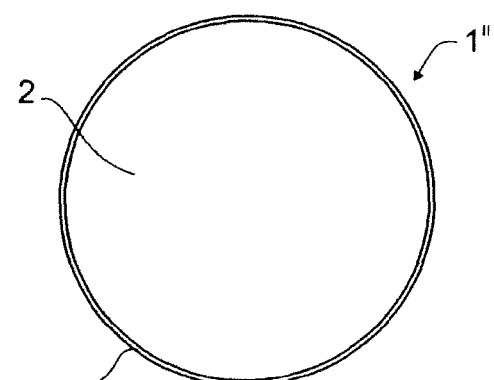

Referring to FIGS. 1a-2b, an elastomeric particle 1, 1', 1" according to the first aspect will now be described. Such an elastomeric particle 1, 1', 1" comprises an elastomeric body 2 and a conducting surface layer 4a, 4b, 6. The conducting surface layer 4a, 4b, 6 may be formed by a plurality of conducting particles 7a, 7b, by deposition of a conducting material 6 (e.g., metal or conducting polymer), or by modifying the conducting properties of the surface of the elastomeric body 2 (e.g., interpenetrating polymer networks with electrically conducting polymer constituents). In the case of conducting particles 7a, 7b, these may be adhered to the elastomeric body 2 by a primer 3. One or more further conductive layers 4b may be provided (as indicated in FIGS. 1a and 2a), and preferably attached to the previous layer 4a by a binder 5.

The size of the elastomeric particle 1, 1', 1" may be in the range of 0.1-250 µm, more preferably in the range of 1-10 µm. The elastomeric particle may have a shape that is regular or irregular. As non-limiting examples, the elastomeric particles may be rod-like, ellipsoidal, spherical, platelets, granules, fibers, porous shells, scaffolding, etc. The elastomeric particles may be hollow or solid. Generally, spherical elastomeric particles may be produced by emulsion or suspension polymerization. Other shapes may be produced by, e.g., cryogenic pulverization or other breakdown processes, such as grinding.

Another way of producing such elastomeric particles is through seed polymerization, which is described in, e.g., JP-A 58-106554 and JP-A 63-191818. Yet another way of producing such elastomeric particles is through emulsion polymerization with additional conditions for creating larger, crosslinked, elastomeric particles, such as is described in U.S. Pat. No. 6,914,100, JP-A 63-191805, JP-A 4323213 and JP-A 10-310603. The polymerization process can be of any type, including radical, polyaddition or polycondensation reactions.

The elastomeric particles may be cross-linked to ensure suitable mechanical properties. It is noted that the references above demonstrate creation of particles that are crosslinked.

In a practical case, it may be convenient to purchase elastomeric particles, which do not have a conducting surface, in wet or dry form from various suppliers, examples of which include Dow Corning, Shin Etsu Chemical and Rohm and Haas for small particles, and several chemical suppliers for larger particles. Naturally, it is also possible to purchase pellets that are to be pulverized or atomized. For example, commercially available thermoplastic elastomer pellets can be heated and spray dried to create smaller particles, or alternatively cryogenically pulverized to produce the same.

The elastomeric body 2 and/or the matrix 11, as will be discussed below, may, as non-limiting examples comprise silicone elastomers, polyurethanes, polybutadiene (specifically high cis polybutadiene), natural rubber, polyisoprene, ethylene-propylene-diene, thermoplastic elastomers, segmented block copolymers, etc. In particular, silicone elastomers have excellent compression set, creep and temperature stability, and can be formulated with excellent fatigue properties, while polyurethanes and polybutadienes can be formulated with excellent dynamic properties (low hysteresis, high resilience, long fatigue life, etc.). Specifically useful are chain-extended PU elastomers with amide chain extenders, with excellent temperature/frequency stability of mechanical properties.

An example of a suitable material is provided in van der Schuur, M, Noordover B, Gaymans R J, 2006, Polyurethane elastomers with amide chain extenders of uniform length. Polymer, 47: 1091-1100.

There are also biomaterials with excellent resilience, such as elastin and resilin, see Elvin C M, Carr A G, Huson M G, Maxwell J M, Pearson R D, Vuocolo T, Liyou N E, Wong D C, Merritt O J, Dixon N E. 2005. Synthesis and properties of crosslinked recombinant pro-resilin. Nature. 437(7061): 999-1002.

In general, the elastomeric body 2 and the matrix 11 may be made from the same family of elastomer, with different degrees of crosslinking or fillers to achieve variations in hardness. One example of an easy to use system is the three-component, variable mix ratio polyurethane system from Crosslink Technology Inc. (disclosed in US 2006/0058456), or their CLC system. Examples of hardening filler materials include quartz, silica, mica, carbon black, etc. These materials are especially suitable for use as fillers in silicone systems.

For the conducting layer 4a, 4b, 6, a range of materials may be used, including metallic or metal oxide conducting species, carbon and structures thereof, conducting polymers etc. Combinations of these materials may also be used.

In case alignment is desirable, the conducting layer 4a, 4b, may include materials from the known groups of paramagnetic, super paramagnetic, or ferromagnetic materials.

In one embodiment, the particles 1, 1',1" may be constructed by layer-by-layer self assembly (LbL-SA) or layer-by-layer covalent self assembly (LbL-CSA) approaches, which produces stronger interlayer bonding than LbL-SA. In this case, the conductive materials (e.g., metallic, metal-oxide, semiconductive or organic) forming the conducting layers 4a, 4b will generally be nanoparticulates 7a, 7b with useful examples being nanoparticles of (including core shell particles) gold, silver, platinum, palladium, copper, nickel, aluminum, chromium, etc. In particular, nanoparticles of gold are easy to produce, and can be stored in a stable configuration before the deposition process.

As one alternative, the conducting layer 4a, 4b, 6 may be provided by electroless deposition, which is a well known method wherein a seed layer (catalyst), such as palladium, is applied to the particles, and further conducting material is deposited via reduction of a metal salt onto the surface of the elastomeric particles. Such a method is described in Mallory G O, Hajdu J B, Electroless plating: fundamentals and applications, American Electroplaters and Surface Finishers Society, Florida, 1990. In such cases a primer 3 may be applied prior to the deposition of the conducting layer.

The elastomeric particles may be somewhat swollen during the application of the conducting layer 4a, 4b, 6, regardless of which type of application technique is selected so that when they are dried, the surface will take on a microscopic texture, in addition the particles will be more suitable for undergoing strain as their surfaces will be wrinkled rather than smooth, since when smooth and too thick, the conductive layers will interfere with the mechanical properties of the particles and can also crack, thereby losing their conductive properties.

As another option, conducting polymers can be electrochemically deposited on the surface of the elastomeric body 2. For example, a thin conducting polymer layer can be deposited so as to produce an inherently conducting layer over the elastomeric particles using in situ oxidization. Such techniques are described within U.S. Pat. No. 5,240,644, U.S. Pat. No. 6,899,829, Gregory R V, Kimbrell W C, Kuhn H H, Synthetic Metals, 28 (1989), pg 823, and Hansen T S, West K, Hassager 0, Larsen N B, Synthetic Metals, 156 (2006), pg 1203.

In the case of LbL-SA or LbL-CSA produced layers, the conductivity of the layers is a combination of quantum tunneling and physical contact between the tightly packed conductive nanoparticles 7a, 7b arranged within the layers over the surfaces of the elastomeric particles 1, 1', 1". This tight knit structure minimally affects the mechanical properties of the elastomeric particle 1, 1', 1". This arrangement also allows the elastomeric particles to maintain surface conductivity even when the entire composite structure is strained.

The fluid environment in which the conductive particles 7a, 7b are constructed must be compatible with the elastomeric particles so that they are not damaged during the assembly process and may be easily transferred from one layering environment to the next without overly demanding intermediate washing and/or drying steps. As mentioned earlier, optimization of the fluid environment can cause advantageous swelling of the elastomeric particles during deposition of the conductive layers.

LbL-CSA or LbL-SA can also be used to form a monolayer on the elastomeric particles, which would be a seed layer, whereupon further conducting material is deposited electrochemically, e.g. by electroless deposition.

Examples of methods for depositing the conducting nanoparticles 7a, 7b onto a surface by self assembly are known from, e.g., US2005/0064204, U.S. Pat. No. 6,025,202, U.S. Pat. No. 6,624,886, U.S. Pat. No. 6,242,264, U.S. Pat. No. 6,458,327, U.S. Pat. No. 6,592,945.

The process of building up multiple conducting layers onto a surface is achieved through repetition of deposition steps, as is disclosed in US2005/0064204 and U.S. Pat. No. 6,458,327. Yet another option for forming the conducting layer 4a, 4b, 6 involves physical vapor deposition processes, a variety of which are known, including vacuum evaporation, sputtering and chemical vapor deposition. Deposition via such methods is considered straight forward, except that one may need to continually mix the elastomeric particles to ensure adequate coverage with the thin conducting material.

The thickness of the conducting layer 4a, 4b, 6 should be as thin as possible, so as not to add to the overall mechanical stiffness of the final particle. This is especially important when using methods that form continuous layers onto the elastomeric particles.

Preferably, the conducting layer thickness may be less than 10% of the diameter of the elastomeric particle. More, the thickness may be less than 5%, less than 1% or less than 0.1% of the diameter of the elastomeric particle.

Expressed differently, the thickness may preferably be less than 500 nm, more preferably less than 100 nm, or less than 50 nm.

For a sensor type embodiment, the layers on the elastomeric body 2 collectively should have an overall quiescent sheet resistance of 0.1-100 k$\Omega$/□, and more preferably a sheet resistance of 1-10 k$\Omega$/□.

For an electrical interconnect application, the layers on the elastomeric body 2 should have an overall quiescent sheet resistance of less than 100$\Omega$/□, more preferably less than 1$\Omega$/□, and most preferably less than 0.1$\Omega$/□.

The primer 3 on the surface of the elastomeric body 2 is selected to initiate the deposition process onto the elastomeric body surface, improve bonding between the elastomeric body and the first conducting layer, and/or to improve bonding of the completed particles to the matrix material. The primer 3 is generally chosen from the known organosilanes and organosiloxanes with examples provided below.

The organosilane compounds include compounds having alkyl and alkoxide groups in one molecule such as hexyltrimethoxysilane, octyltrimethoxysilane, cyclopentyltrimethoxysilane and cyclohexyltrimethoxysilane; organosilane compounds having vinyl and alkoxide groups in one molecule such as vinyltrimethoxysilane; organosilane compounds having amino and alkoxide groups in one molecule such as (N,N-dimethylaminopropyl)trimethoxysilane, (N,N- diethylaminopropyl)trimethoxysilane, aminopropyltrimethoxysilane, N-(6-aminohexyl)aminopropyltrimethoxysilane, and (aminoethylaminomethyl)-phenethyltrimethoxysilane; compounds having ammonium and alkoxide groups in one molecule such as N,N,N-trimethylammoniopropyltrimethoxysilane; organosilane compounds having heteroaromatic ring and alkoxide groups in one molecule such as 2-(trimethoxysilylethyl)pyridine; organosilane compounds having fluoroalkyl and alkoxide groups in one molecule such as (3,3,3-trifluoropropyl)trimethoxysilane and (decafluoro-1,1,2,2-tetrahydro-ooctyl)triethoxy silane; organosilane compounds having polyethyleneglycol and alkoxide groups in one molecule such as N-(triethoxysilylpropyl)-O-po-lyethyleneoxide-urethane; organosilane compounds having thiocyanate and alkoxide groups in one molecule such as 3-thiocyanatepropyltriethoxysilan-e; organosilane compounds having ether and alkoxide groups in one molecule such as 3-methoxypropyltrimethoxysilane; organosilane compounds having thiol and alkoxide groups in one molecule such as 3-mercaptopropyltrimeth-oxysilane; organosilane compounds having halogen atom and alkoxide groups in one molecule such as 3-iodopropyltrimethoxysilane and 3-bromo-propyltrimethoxysilane; organosilane compounds having epoxy and alkoxide groups in one molecule such as 5,5-epoxyhexyl-triethoxysilane; organosilane compounds having sulfide and alkoxide groups in one molecule such as bis[3-(triethoxysilyl)propyl]tetrasulfide; organosilane compounds having hydroxyl, amino and alkoxide groups such as bis(2hydroxyethyl)-3-amino-propyltriethoxysilane; organosilane compounds having an amino group and groups derived by hydrolysis of alkoxide groups in one molecule such as aminopropylsilane triol; organosilane compounds having alkyl group and chlorine atoms in one molecule such as octyltrichlorosilane, cyclotetramethylenedi-chlorosilane, (cyclohexylmethyl))trichlorosilane, cyclohexyl-trichlorosilane, and tert-butyltrichlorosilane; organosilane compounds having fluoroalkyl group and chlorine atoms in one molecule such as (decafluoro-1,1,2,2-tetr-ahydrooctyl)tri-chlorosilane and (3,3,3-trifluoropropyl)trichlorosilane; organosilane compounds having heteroaromatic ring and chlorine atoms in one molecule such as 2[2-(trichlorosilyl)-ethyl]pyridine; and organosilane compounds having an aromatic ring and chlorine atoms in one molecule such as phenethyltrichlorosilane. See, e.g., US 2005/0064204.

Organosiloxane compounds generally include alkoxy-silanes such as methyltrimethoxysilane, vinyltrimethoxy silane, 3-glycidoxypropyltrimethoxysilane, 3-methacryloxypropyltrimethoxysilane, dimethyldimethoxysilane, trimethylmethoxysilane, trimethylethoxysilane, tetramethoxysilane, and tetraethoxysilane; siloxane oligomers such as silanol-endblocked dimethylsiloxane oligomers, silanol-endblocked dimethylsiloxane/methylvinylsiloxane cooligomers, silanol-endblocked methylvinylsiloxane oligomers, silanol-endblocked methylphenylsiloxane oligomers, 1,3,5,7-tetramethylcyclotetrasiloxane, and 1,3,5,7,9-pentamethylcyclopentasiloxane; polyorganosiloxanes ranging from low-viscosity liquids to gums, and including but not limited to trimethylsiloxy-endblocked polydimethylsiloxanes, trimethylsiloxy-endblocked dimethylsiloxane/methylvinylsiloxane copolymers, trimethylsiloxy-endblocked dimethylsiloxane/methylphenylsiloxane copolymers, trimethylsiloxy-endblocked polymethylhydrogensiloxanes, trimethylsiloxy-endblocked dimethylsiloxane/methylhydrogensiloxane copolymers, silanol-endblocked polydimethylsiloxanes, silanol-endblocked dimethylsiloxane/methylvinylsiloxane copolymers, silanol-endblocked dimethylsiloxane/methylphenylsiloxane copolymers, silanol-endblocked polymethylhydrogensiloxanes, silanol-endblocked dimethylsiloxane/methylhydrogensiloxane copolymers, dimethylvinylsiloxy-endblocked polydimethylsiloxanes, dimethylvinylsiloxy-endblocked dimethylsiloxane/methylvinylsiloxane copolymers, dimethylvinylsiloxy-endblocked dimethylsiloxane/methyl phenylsiloxane copolymers, dimethylhydrogensiloxy endblocked polymethylhydrogensiloxanes, and dimethylhydrogensiloxy-endblocked dimethylsiloxane/methylhydrogensiloxane copolymers; and silicone resins, including but not limited to resins composed of $R_3SiO_{1/2}$ and $SiO_{4/2}$ units, silicone resins composed of the $RSiO_{3/2}$ unit, resins composed of the $R_2SiO_{2/2}$ and $RSiO_{3/2}$ units, and resins composed of the $R_2SiO_{2/2}$, $RSiO_{3/2}$, and $SiO_{4/2}$ unit. See, e.g., U.S. Pat. No. 7,074,849.

Further organosilanes with functional groups including: epoxy, amino, ketimino, vinyl, methacryloxy, acryloxy, mercapto, polysulfido, isocyanato, styryl and hydrolysable groups including chloro, methoxy, and ethoxy functional groups. See Shin Etsu Chemical silane coupling agent brochure for similar listings.

In practice, a particular agent is generally selected based on consultation of the literature, and simple adhesion trials. In general, the coupling agents are selected such that the coupling agents have organic functional groups that match the reactivity of the polymer surface in question.

Known examples include aminopropyltriethoxysilane or mercaptopropyltrimethoxysilane (depends on the base material being bonded to), as disclosed in US2005/0064204 or U.S. Pat. No. 6,458,327 for glass substrates, but groups can be selected for the appropriate elastomer materials in question.

There are also proprietary, commercially available primers available from such companies as Dow Corning, Shin Etsu Chemical, Nusil, among others.

The binding layer 5 is used to bond together subsequently deposited conducting layers. As examples of binders for LbL-SA, materials containing two functional groups such as hydroxyl groups, amino groups, carboxyl groups, carboxylic acid anhydride groups, mercapto groups, hydrosilicon groups and combinations thereof may be used, as described in US2005/0064204. The selected material should have at least one functional group that can covalently or non-covalently bond to the desired molecule, such as the nanoparticle or the elastomer.

Another name for these materials are ligands, containing one or more amino groups, thiol groups, and are chosen from the group comprising mercaptoalkylsilanes, aminoalkylsilanes, dimercaptoalkanes, diaminoalkanes, hydroxy-alkanes, carboxy-alkanes, dihydroxy alkanes, and dicarboxyalkanes, as disclosed in U.S. Pat. No. 6,458,327.

As an example for polyurethane/gold nanocomposites, mercaptoethanol may be used as the binding agent.

As an example for a polysiloxane/silver nanocomposite, polysiloxane may be used as the binding agent. Specifically, poly(dimethyl-co.methylhydrido-co-3cyanopropryl,methyl) siloxane. The same polysiloxane as used for the elastomeric materials of the composite may be used directly as the binder (without primer), so as to reduce the overall number of materials in the composite.

As an example for building up multiple gold nanoparticle layers, 2-mercaptoethanol or 2mercaptoethylamine may be used, see US2005/0064204.

Another example for building up multiple layers of gold nanoparticles with dodecylamine stabilizing ligands would be mercaptoalkylsilanes, aminoalkylsilanes, dimercaptoalkanes, diaminoalkanes, or polyfunctionalized polymers, as disclosed in U.S. Pat. No. 6,458,327.

Referring to FIGS. 4-6b, the above described elastomeric particles having a conducting surface may be used to provide a pressure sensor element.

FIG. 4 schematically illustrates a first embodiment of a pressure sensor element 20. The drawing is magnified, and the vertical direction V is greatly exaggerated. The measurement side is indicated by reference numeral 310. The sensor element 20 is based on a substrate 21, upon which a pair of electrodes 22a, 22b are arranged. The electrodes may, but do not need to, be co-planar. Electrodes 22a, 22b may be provided by patterning a conducting material onto the substrate/first elastomeric portion in any known manner. A first non-conducting elastomeric portion 23 is arranged between the electrodes. The first elastomeric portion 23 may cover opposing edge portions of the electrodes 22a, 22b and it may have a maximum thickness which is larger than that of the electrodes. The thickness of the first elastomeric portion 23 may taper or otherwise diminish towards its edges.

On the first elastomeric portion 23, one or more conducting layers 24 may be arranged. Such conducting layers may comprise elastomeric particles as described above, which are arranged in a matrix comprising a primer and/or a binder as described above. The conducting layers 24 are in contact with the electrodes 22a, 22b. In particular, a primer 3, such as the ones mentioned above, may be used between the first elastomeric portion 23 and the first conducting layer 24, and a binder 5, such as the ones mentioned above, may be used between the first conducting layer 4a and further conducting layers 4b.

A second non-conducting elastomeric portion 25 may be arranged on top of the conducting layers 24, such that the conducting layers 24 are enclosed by the first and second elastomeric portions 23, 25 with only edge portions of the conducting layers 24 being exposed to the electrodes 22a, 22b. Another primer or binder may be used between the conducting layers 24 and the second elastomeric portion 25. The elastomeric portions 23, 25 may be formed from any material mentioned above with respect to the elastomeric body 2.

The sensor element, including the elastomeric portions 23, 25, the electrodes and the conducting layers 24 may be enclosed in an isolation coating 26, which may be non-conducting. The isolation coating 26 may be made from an elastomeric material and may optionally be foamed.

In one embodiment, the elastomeric portions 23, 25 are made from elastomeric materials having different modulus of elasticity. In another embodiment, the elastomeric portions 23, 25 are made from elastomeric materials having substantially the same modulus of elasticity.

When the sensor element 20 is subjected to pressure (typically compression in the vertical direction V), the relative positions of the particles present in the conducting layers 24 will change, thereby changing the impedance of the sensor element, as measured over the electrodes 22a, 22b.

The sensor element 20 may be produced according to the following.

A substrate 21 with electrodes 22a, 22b is prepared and possibly cleaned. Such a substrate may, e.g., be a fabric or a polymer film. A primer may be applied to the surface where the first elastomer layer 23 is to be deposited. A first elastomer layer 23 with a first hardness is deposited. A primer layer, with a primer as described above, may then be deposited. Conductive layers 24 are deposited to bridge the electrodes 22a, 22b and to extend out past the first elastomer 23. Binder layers 5 as described above may be arranged between the conductive layers 24. Another primer may be used to coat the conductive layers 24. A second elastomer layer 25 with a second hardness is deposited. This second elastomer layer 25 can also function as a mechanical isolation layer. Optionally, an isolation coating 26 is deposited, and optionally foamed. This isolation coating 26 also may function as a stress filtering layer to smooth out contact stresses applied to the sensor element in the vicinity of the first and second elastomer layers 24, 25.

FIG. 5 illustrates an alternative embodiment of a sensor element 20', wherein the first elastomer 23' has been dispensed on the substrate 21 prior to the forming of the conducting layer 24 and the electrodes 22a', 22b'. The conducting layers 24 and/or the electrodes 22a', 22b' may be patterned, e.g., dispensed, printed or jetted, onto the substrate and onto the first elastomer 23'.

FIG. 6a illustrates another alternative embodiment of a sensor element 20", wherein the first elastomer 23" has been molded onto the substrate. Subsequently, the conducting layers 24 have been formed, and thereafter the electrodes 22a", 22b" have been printed.

Referring to FIG. 6b, there is illustrated a detail on how the conducting layer 24 may be formed. In one embodiment, the conducting layer 24 comprises one, two or more layers of the elastomeric particles 1, 1', 1" described above with reference to FIGS. 1a-2b. The conducting layer 24 according to this embodiment may be produced by applying a primer 3 in a desired pattern where the conducting layer 24 is to be formed. Thereafter, conducting particles 1, 1', 1" are applied so as to form a first conducting layer 4a. A binder 5 is thereafter applied in a desired pattern, after which further conducting particles 1, 1', 1" may be applied so as to form a second conducting layer 4b. This method may be used to provide the conducting layer of any of the embodiments illustrated in FIGS. 4-6b.

In another embodiment, the conducting layer 24 of FIGS. 4-6b may be formed in the any of the manners described with reference to the conducting surface of the elastomeric particles 1, 1', 1" of FIGS. 1a-2b. Thus, the conducting layer 24 may be formed using primer 3 and/or binders 5 as described with reference to FIGS. 1a-2b to provide one, two or more layers 4a, 4b of non-elastomeric conducting particles 7a, 7b. The technology disclosed in US 2005/0064204A1 may be used to provide the conducting layer.

It is noted that alternatively, the conducting layer 24 may be formed by patterning a compound for forming the composite material described below, possibly after deposition of a primer.

Figure 3:
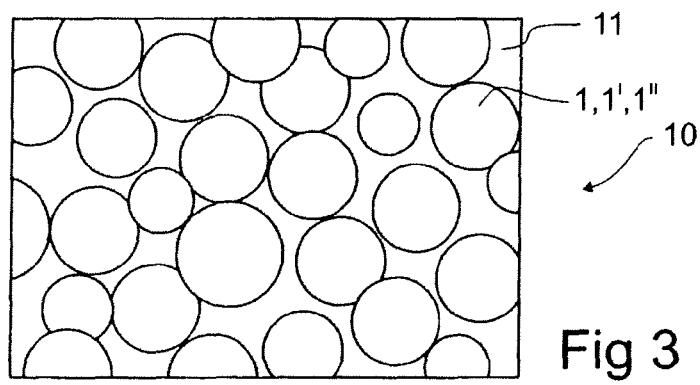
FIG. 3 is a schematic view of a compound according to the present disclosure.

FIG. 3 schematically illustrates a composite material 10 comprising elastomeric particles 1, 1', 1" as described above and a matrix material 11.

The above described elastomeric particles 1, 1', 1" may thus be used to provide a composite material 10, which in turn may be used for forming pressure sensor elements. Such a composite material may be formed by mixing the elastomeric particles with a matrix material 11, which may also be an elastomeric material.

In practice, the matrix material may be substantially the same as that of the elastomeric body 2 of the particles, however, with a different hardness or modulus of elasticity. Examples of suitable matrix materials are thus given above with reference to the elastomeric particle 2.

By using a composite comprising soft elastomeric particles 1, 1', 1", it is possible to better manage strain related damage, quiescent electrical impedance and strain sensitivity of the electrical impedance within the composites by improving and managing stresses at interfaces between matrix and particles, and within the matrix.

The composite material thus comprises soft particles 1, 1', 1" (elastomeric in nature) of a first modulus of elasticity, the surfaces of which are made conductive (as described above), mixed with a binder material (elastomeric in nature) of a second modulus of elasticity into a composite structure. The composite material may also contain coupling agents, compatibilizing agents and other particulates, etc. to fine tune the final composite properties.

The coupling agents or compatibilizing agent may be chosen from the known organosilanes and organosiloxanes with examples mentioned above.

Interfacial stresses and strain related damage may be minimized when the first and second moduli of elasticity are chosen to be substantially equivalent to each other. Such an arrangement produces a composite with low mechanical hysteresis, and low impedance strain sensitivity while further improving the cycle life of the composite and improving linearity of the strain-impedance relationship of the composite.

Finite quiescent impedance can be set during fabrication via alignment, volumetric ratios of constituents and fabrication conditions (solvents, compression, temperature profile during curing, etc).

Pressure sensitivity may be determined primarily by the equivalent modulus of elasticity, the strain-impedance relationship of the composite, and the structure of the sensor built from the composite (geometry, field orientation, electrode placement, etc.).

Strain sensitivity can be increased in a controlled manner by changing the ratio between the first and second moduli of elasticity.

The soft elastomeric particles 1, 1', 1" can be mixed randomly with a matrix-forming material (and other particles) or used in conjunction with preferential alignment (see below).

Alignment, as will be further discussed below, can be used to further affect strain sensitivity of the electrical impedance of the composite.

The mechanical properties of the overall system are primarily related to the mechanical properties of the constituent components (particles, matrix, and the difference between the two), the mix ratios, alignment configurations, as well as the strength of the bonds between the particles and the matrix.

The pressure sensitivity of the electrical impedance is then a function of the strain sensitivity and the mechanical properties of the composite.

A mixture or compound 10 (see FIG. 3) comprising elastomeric particles 1, 1', 1" and matrix-forming material 11 may be provided. The compound may be in the form of a paste. The matrix-forming material may be allowed to harden or set into any of the materials mentioned above as being suitable for the elastomeric body 2 or matrix 11, or similar/equivalent materials. Such a compound may be, e.g., printed or deposited in order to provide sensor elements as illustrated in FIGS. 4-10 and then allowed to harden or set. Curing may be facilitated in any way known to the skilled person, such as by influence of radiation, etc.

In the composite material arranged with generally randomly distributed soft elastomeric particles, the volume percent of coated particles into a matrix, for randomly distributed particle systems, will generally be in the range of 10-75% by volume. This is in line with the volume percent of prior art sensory materials.

In cases of alignment, as described below, generally the required volume percent of particles may be reduced by a factor of 10 to 100. This will further benefit the mechanical properties of the resulting composite as the reduced amount of interfaces will further reduce mechanical hysteresis during use.

Referring to FIGS. 7-10, the description will now be focused on sensor elements using a composite material as described above.

Figure 7:
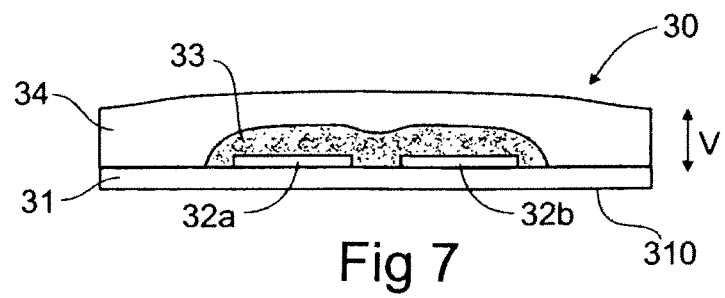
FIG. 7 is a schematic cross-sectional view of a sensor element according to the first type of embodiment of the present disclosure.

FIG. 7 schematically illustrates a first embodiment of a sensor element 30, wherein a substrate 31 is provided with electrodes 32a, 32b. A conductive composite 33, such as the one described above, is then provided on the substrate and in contact with the electrodes. Optionally, an isolation coating 34, such as the ones described with respect to FIGS. 4-6b, may be provided to encapsulate the sensor element 30.

Figure 8:
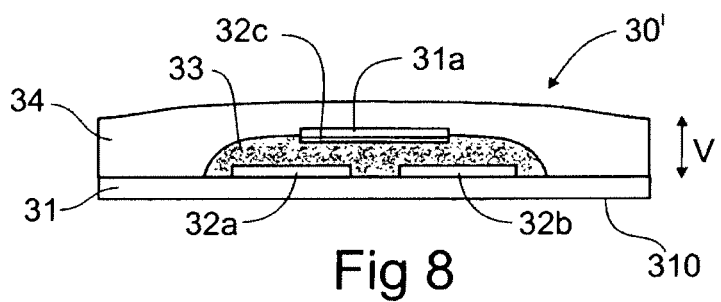
FIG. 8 is a schematic cross-sectional view of a sensor element according to the first type of embodiment of the present disclosure.

FIG. 8 schematically illustrates a second embodiment of a sensor element 30', which is similar to the one of FIG. 7, but provided with a second substrate 31a, with a third electrode 32c. The second substrate is spaced from the first substrate, and may be "floatingly" arranged in the composite material 33. The second substrate 31a with its associated electrode may be produced in the same way as the first substrate 31. The third electrode 32c can be used to facilitate preferential alignment within the composite material 33 during fabrication, augment the electrical impedance of the sensor element 30, provide more suitable area within the composite material 33 where impedance measurements can be taken, preferentially spread applied stress over the composite material 33, provide a means of measuring pressure gradients applied to the sensor element 30, or electrically shield the sensor element 30 from the surroundings.

Figure 9:
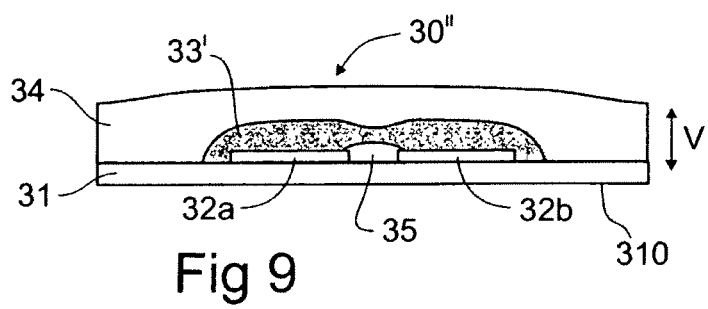
FIG. 9 is a schematic cross-sectional view of a sensor element according to the first type of embodiment of the present disclosure.

FIG. 9 schematically illustrates a third embodiment of a sensor element 30", wherein a non-conducting elastomeric portion 35 is provided between the electrodes 32a, 32b in a manner similar to that of FIG. 4 or 5, e.g., in order to reduce stress concentrations around the edges of the electrodes, to control stresses in the composite material 33', to separate the stress and field concentrations within the composite material 33' and/or to facilitate preferential alignment in the composite material 33' during fabrication of the sensor element 30". The elastomeric portion 35 may be further foamed to alter the hardness and the Poisson's ratio of this portion of the sensor element 30". This provides a further means of controlling pressure sensitivity of the sensor element 30"

Furthermore, in FIG. 9, the portion of the composite material 33' extending between the electrodes 32a, 32b may be structured, e.g., made narrower, so as to further control sensitivity of the electrical impedance of the composite material 33' to applied pressure, and locally alter the mechanical properties of the composite material 15 33'.

In the embodiment of FIG. 9, a third electrode with substrate as described with reference to FIG. 8 may be included.

Figure 10:
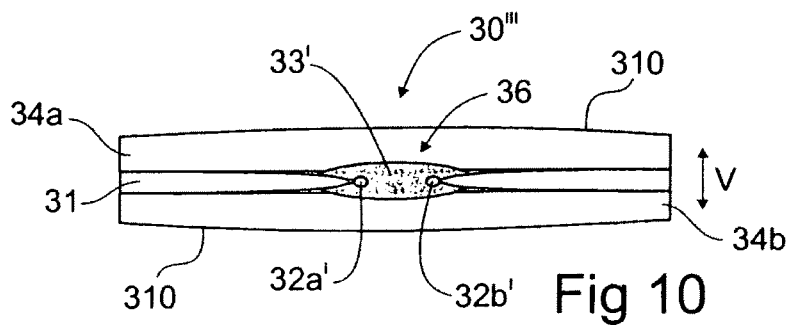
FIG. 10 is a schematic cross-sectional view of a sensor element according to the first type of embodiment of the present disclosure.
Figure 11:
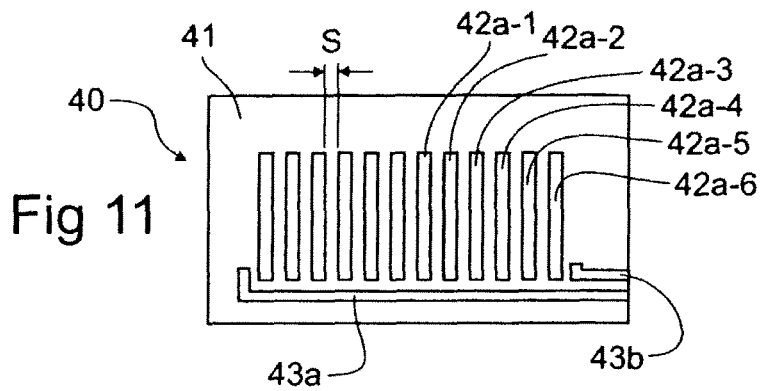
FIGS. 11-14 are schematic views of layers forming part of a sensor element according to a second type of embodiment of the present disclosure.
Figure 12:
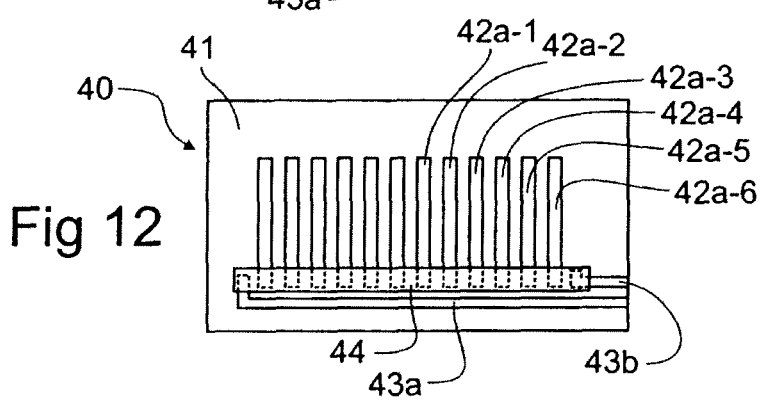
Figure 13:
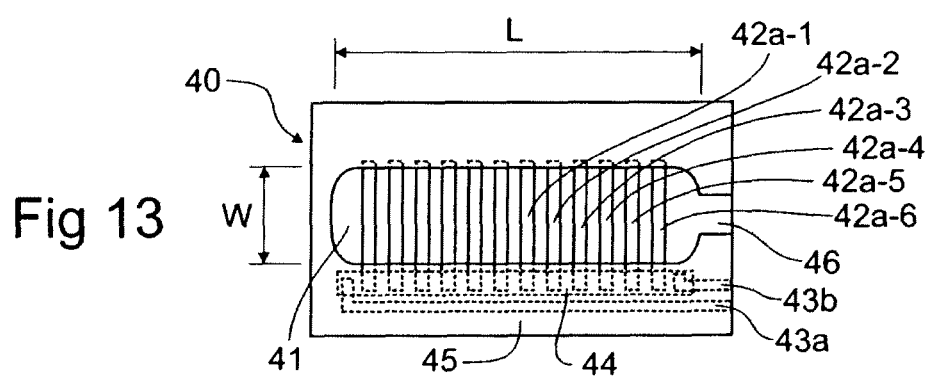
Figure 14:
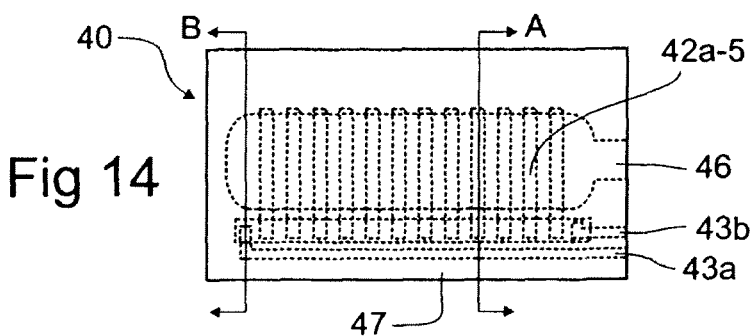
Figure 15:
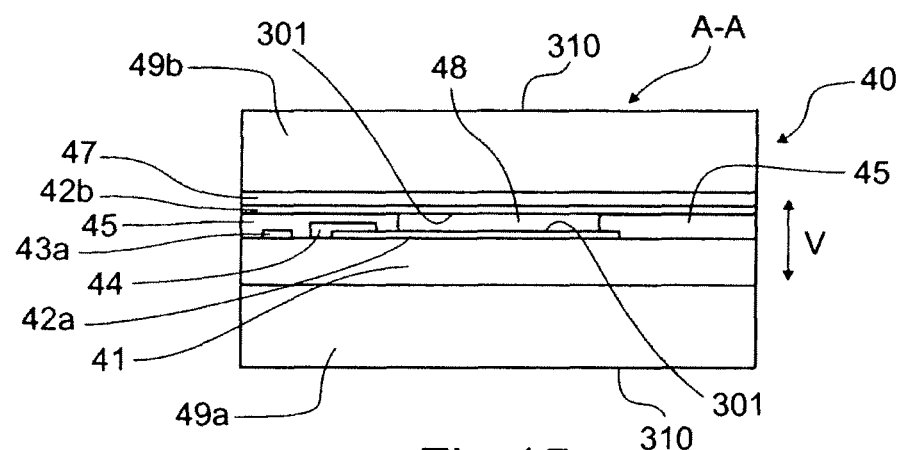
FIGS. 15 and 16 are cross-sectional views of the sensor element of FIGS. 11-14.
Figure 16:
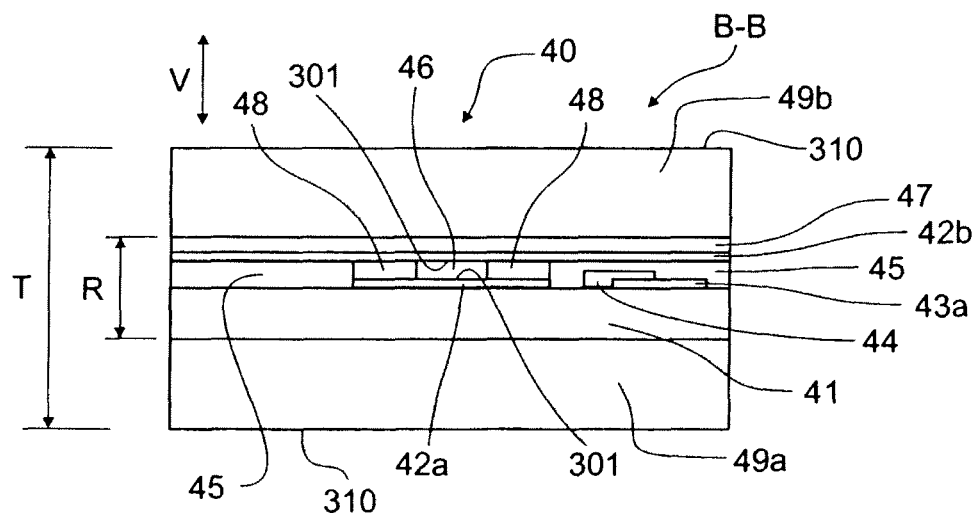

FIG. 10 schematically illustrates a fourth embodiment of a sensor element 30''', which is arranged in a through hole 36 in the substrate 31. Such a substrate may, e.g., be a fabric or a polymer film. The composite material 33" may be symmetrically arranged in relation to the substrate 31. Electrodes 32a', 32b' may be provided by a wire embedded in or arranged on the substrate 31, or as a conductive yarn provided in a fabric. Electrodes 32a', 32b' may also be provided by patterning a conducting material onto the substrate in any known manner. In the latter case, the wires leading to the electrodes may be provided with an isolating coating, which is removed to expose the conducting part to thereby provide the electrodes 32a', 32b'. Such removal may be achieved by, e.g., etching, solvent, mechanical ablation, etc. This embodiment is particularly suitable for creating very thin sensor systems.

In this embodiment, isolation coatings 34a, 34b may be provided on both sides of the substrate 31, such as to encapsulate the sensor element.

In the embodiment of FIG. 10, the third electrode with or without associated substrate, as described with respect to FIG. 8 may be provided.

In the embodiments of FIGS. 7-10, the composite material may optionally be foamed, in a per se known manner.

A production process for providing the sensor element of FIGS. 7-10 may include providing a suitable substrate material; providing electrodes on the substrate, e.g., by a patterning process; depositing a mixture for forming the composite material (including elastomeric particles and matrix material); optionally providing a field application fixture and apply the requisite fields (AC, DC, ramp-up, hold, ramp-down) for alignment; curing the matrix material (e.g., by application of UV light, heating, etc.); removing any alignment field; optionally post curing the matrix material; and removing any remaining alignment field, if not removed early in the curing process. Optionally, conductive bridges between sensors and external electronics may be provided, e.g., by printing, lithographic patterning, etc.

It is recognized that there are many electrode and magnet arrangements for alignment as well as mechanical layouts that may be optimized for this type of sensor.

It is noted that for the embodiments described with reference to FIGS. 4-10, the electrodes may be a conducting compound, metal or conducting organic material. Application methods include PVD, CVD, electrochemical methods, ink-jetting, printing etc., followed by any necessary sintering or drying steps.

Substrate materials for providing the substrate of the embodiments disclosed with reference to FIGS. 4-10 include films (preferably biaxially oriented polymer films including polyethylene terephthalate, polyethylene naphthalate, but also polymer films including polycarbonate, polyamide, polyimide, nylon, polyethersulfone, aromatic fluorine-containing polyarylates, etc.), fabrics (both woven and nonwoven), felts, apertured films and foams (such as PU foam).

As indicated above, in the embodiments illustrated with reference to FIGS. 4-10, it is possible, and sometimes desirable, to preferentially align the elastomeric particles of the composite between the electrodes during fabrication. Motives for so doing include reducing the volume fraction of particulate in the conducting elastomer composite. This process may improve two important aspects of the sensor properties: (i) hysteresis is improved due to the fact that fewer interfaces are present to form stress concentrations throughout the composite material, and (ii) the elastomeric particles may be localized only to the regions of the sensor where they are needed. Furthermore, alignment allows for the monitoring and control of the quiescent impedance of the sensors during fabrication and aging (post fabrication), thereby increasing yield and more tightly controlling the final properties of the sensors.

In the same regard, alignment can allow individual sensors within a cluster or garment to be adjusted so as to be similar to each other within each final product. It may also allow flexibility in terms of calibrating some sensors within a garment to behave with different quiescent impedance than others for various applications.

For example, it may be possible to provide a composite, where all sensor elements are tuned to have a quiescent impedance of 10 kohm under application-like test conditions.

As another example, some sensor elements may be tuned to behave more like switches with high sensitivity (for determining garment state, e.g., donned, removed), while others maintain lower sensitivity (for making accurate measurements during treatments).

The alignment discussed above may most easily be performed using B-fields, E-Fields, or combinations thereof during the fabrication of the sensor element.

Of course, to use B-fields, the particles should have a suitably high magnetic permeability, such that they can move within the composite upon the application of an external field.

E-field systems will work for any particle types. It may be preferable that an AC field is used and that the application frequency is sufficiently high, such that the field does not collapse (breakdown) if a solid chain of particles is formed between the electrodes. Field collapse is not good in general, as it prevents surrounding particles from forming chains within the composite of the sensor, i.e., without control of E-field collapse, one gets only a single connection between electrodes that is very fragile in practice.

For E-field systems, it is also possible to use a soft barrier layer around the elastomeric particles, such that the breakdown effect will not be as dramatic, i.e., as particles come together into chains, the impedance drops more gradually and therefore breakdown of the field does not occur suddenly as can happen with purely conducting fillers. Such a barrier layer can be formed by a primer layer applied to the external surface of the particles before mixing them with the matrix. For some matrix material, and conducting layer combinations, such a barrier layer is formed naturally such as is the case for silicone matrices and nickel conducting layers.

For both types of fields, in situ stirring is possible using rotating fields. This can be useful for slowly guiding particles into position without creating strong single chains and will generally result in more particles forming along the desired pathway than with only one field element applied between the requisite electrodes.

The electrodes applying the field may be the sensor electrodes themselves, but they may also be separate electrodes provided in a manufacturing fixture or mold.

Combination of fields may be useful as the presence of one field can significantly reduce the requirements for the other field. For example, permanent magnets may establish a B-field in the vicinity of the sensor element electrodes, whereby particles begin movement towards the electrodes due to the presence of the B-field. Then an E-field applied at the electrodes may be used to finish the alignment process with much lower voltage requirements, e.g., dropping the voltage requirement by a factor of 10-100 times.

Passive structures can also be printed onto the sensor to guide the particle traces and further assist with the alignment process. For example, a printed elastomer layer, between electrodes, with different hardness than the conducting elastomer blend, may be printed such that when an E-field is applied to the electrodes, particles align primarily from the centers of the electrodes rather than the edges. This prevents collocation of field concentrations between the test E field and stress fields in the sensor during operation, thus improving repeatability within the sensor element. An example of such an elastomer is shown in FIG. 9.

Referring to FIGS. 11-22, another type of sensor element 40 will now be described. This type of sensor element may be used on its own or in combination with the sensor elements 20, 30 described above.

The sensor element 40, 40', 40'', 40''', 40$^{IV}$, 40$^{V}$, 40$^{VI}$, 40$^{VII}$ and associated embodiments as described in the following are advantageous as sensor elements in that they have improved mechanical response and aging characteristics, immunity to EMI, and the ability to be used for inline calibration of compression systems.

This type of sensor can be most basically be characterized as an array of contact switches with pressure defined switching levels.

Referring to FIGS. 11-16, the sensor element 40 comprises a first substrate 41 with patterned metallic electrodes 43a, 43b, 42a-1, 42a-2, 42a-3, 42a-4, 42a-5, 42a-6, a spacer 45, and a second substrate 47 with patterned metallic electrodes 42b, wherein the first electrodes comprises an array of electrode elements 42a-1, 42a-2, 42a-3, 42a-4, 42a-5, 42a-6, which are separated from each other by a spacing S. A resistive element 44 forming a conduction path is arranged on the first substrate 41, such that the electrode elements 42a-1, 42a-2, 42a-3, 42a-4, 42a-5, 42a-6 contact the resistive element 44 at different portions along the conduction path. Connector electrodes 43a, 43b are provided at spaced apart portions of the resistive element 44, typically at end portions of the conduction path.

The second substrate 47 is arranged substantially parallel with the first substrate 41, and spaced from the first substrate 41 by the spacer 45. On the second substrate 47, there is a second electrode 42b, which is spaced from and faces the first electrode 42a. The second electrode 42b may be formed as a continuous sheet, the extent of which substantially coincides with an effective overall extent of the first electrode 42a-1, 42a-2, 42a-3, 42a-4, 42a-5, 42a-6.

The spacer 45 forms a cavity 48 between the first and second substrates 41, 47. This cavity may be vented, so as to equalize air pressure inside and outside the sensor element.

The cavity 48 need not be rectangular or circular in shape. It can be formed into many shapes including, rectangles, circles, ellipses, dumb-bell like shapes, polygons, and perturbations thereof. Circles are useful for minimizing stresses at the edges of the cavity 48, while rectangles are easily patterned by standard manufacturing processes.

In one embodiment, the resistive element is arranged outside or adjacent the cavity. Hence, the resistive element need not contact the movable parts of the electrode(s), which decreases its sensitivity to wear.

Figure 17:
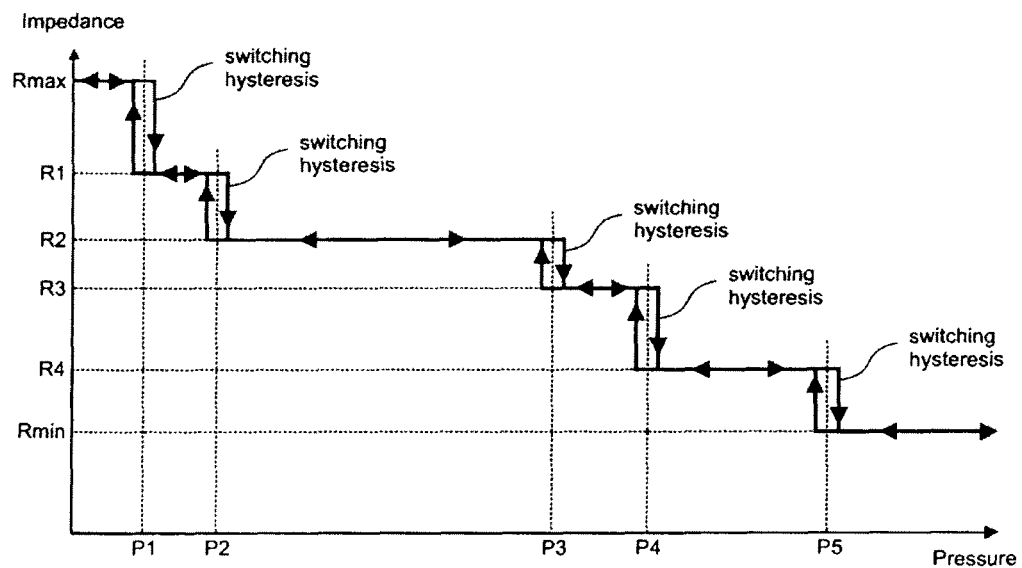
FIGS. 17-18 are diagrams illustrating the behavior of the sensor element of FIGS. 11-16.

When the sensor element 40 is subjected to pressure, the first and second substrates 41, 47, and thereby also the first and second electrodes 42a-1, 42a-2, 42a-3, 42a-4, 42a-5, 42a-6, 42b, are pressed towards each other, so that an area of contact between the first and second electrodes 42a-1, 42a-2, 42a-3, 42a-4, 42a-5, 42a-6, 42b is provided. The area of contact will increase continuously, as more pressure is applied. As the area of contact increases, more and more of the first electrode elements 42a-1, 42a-2, 42a-3, 42a-4, 42a-5, 42a-6 will become "short circuited" by the second electrode 42b, thereby providing a shunt path past the conduction path provided by the resistive element 44. Hence, the impedance of the sensor element 40 will decrease stepwise as a function of the applied pressure. This is illustrated in FIG. 17, which illustrates a behavior of an embodiment with a number of first electrode elements 42a-1, 42a-2, 42a-3, 42a-4, 42a-5, 42a-6 that successively contact the second electrode 42b, so as to shunt the resistive element 44 to decrease the overall impedance of the sensor 40.

The elements of the first electrode 42a-1, 42a-2, 42a-3, 42a-4, 42a-5, 42a-6 are patterned such that they are shunted at the appropriate pressure levels. For example, for an application which requires that the patient is subjected to 10 mmHg±3 mmHg for some time period, followed by 50 mmHg±5 mmHg, and the overall pressure applied should not exceed 70 mmHg, the traces could be arranged such that shunting occurs at 7 mmHg, 13 mmHg, 45 mmHg, 55 mmHg, and 70 mmHg. Another alternative would be that the traces are arranged such that shunting occurs at 10 mmHg, 50 mmHg and 70 mmHg.

Hence, points of discontinuity between the pressure and impedance relationship of the pressure sensor element 40 may be determined by the number of first electrode elements 42a-1, 42a-2, 42a-3, 42a-4, 42a-5, 42a-6, their size and relative position with respect to each other and within the cavity 48, as well as the thickness of the spacer 45, the mechanical properties of the first and second substrates 41, 47 and the overall dimensions of the cavity 48. In embodiments with a large number of first electrode elements, the sensor element 40 will more closely approximate an analog relationship between impedance of the conduction path and the applied pressure.

The resistive element 44 may be formed as a patterned resistive trace (e.g., by means of printing, vacuum evaporation, thermal transfer printing, etc.) or as an array of discrete elements. This resistive element may be arranged outside the flexible part of the sensor element 40. The resistive element 44 may most easily be provided by printing using traditional resistive inks or pastes. The resistive element 44 will generally be encapsulated or covered by the spacer layer 45, such that it is not subjected to significant pressure application during typical operations, and thus the resistance of the resistive element 44 will not vary significantly during operation. Stiff, well characterized inks and pastes can be used for the resistive element 44 to ensure that suitable properties are maintained during use. In addition, due to the discontinuous nature of the pressure-impedance relationship for such a sensor, moderate variations in the resistance of the resistive element 44 can be easily tolerated over the life of the sensor 35 element 40 without degradation of performance.

The manner in which the elements of the first electrode 42a-1, 42a-2, 42a-3, 42a-4, 42a-5, 42a-6 are connected to the resistive element 44 can be a serial connection, parallel or any combination thereof. Full advantage of connection possibilities can be used to optimally shape the pressure-impedance relationship of 5 the sensor element 40.

In addition, in the case where the resistive element 44 is made from several individual resistor elements, these need not be equal to one another. For example, in the above case, the resistance change for the shunt at 7 mmHg may be significantly smaller than that at 13 mmHg, so as to most clearly define the output resistance around the desired operating point. This may be useful when the device is operated in very hostile electromagnetic environments.

The sensor element 40, 40', 40", 40''', 40'''', $40^{IV}$, $40^{V}$, $40^{VI}$, $40^{VII}$ may be built from structurally sound materials, such as biaxially oriented films, and metallic, carbon, or metal oxide layers, which are thin and deposited from pure materials (no particulate based inks, etc. are needed). The spacer may be attached directly to the adjacent membranes without pressure sensitive adhesives or other creep prone materials, e.g., by welding. This ensures that the creep and other undesirable mechanical effects are minimized within the flexible components of the sensor element 40, 40', 40", 40''', $40^{IV}$, $40^{V}$, $40^{VI}$, $40^{VII}$.

The substrates 41, 47 may be in the form of membranes of biaxially oriented films of engineering polymers. Primarily, biaxially oriented polymer films, such as polyethylene terephthalate, polyethylene naphtha late and also polymer films including polycarbonate, polyamide, polyimide, nylon, polyethersulfone, aromatic fluorine-containing polyarylates may be used. Membrane thickness is generally less than 25 micron, preferably less than 10 micron, most preferably 2-5 micron.

Electrodes 42a-1, 42a-2, 42a-3, 42a-4, 42a-5, 42a-6, 42b, 43a, 43b may be formed by patterning onto the substrate 41, 47 using physical or chemical vapor deposition techniques. Typical conducting materials for electrodes may be silver, gold, copper, aluminum, titanium, chromium, nickel, etc. Alternatively, electrodes may be provided by conductive films and may be patterned using electroless deposition, electrochemical deposition, LbL self assembly and other techniques known in the art. It may be advantageous if the electrodes are at least partially composed of multiple layers. A base layer may be a compatibilizing layer, such as Cr, Ti, NiCr to improve adhesion to the substrate 41, 47, a second layer may be a highly conducting layer, and an upper layer may be a protective layer.

It is possible to deposit a thin overcoating layer 301, to protect one or both of the electrodes from damage due to repeated contact during operation. One example of a suitable material for an overcoating layer would be graphite, another would be chrome or chrome alloys. Such top layers can be applied via PVD, CVD, electrochemical or self assembled means.

The electrodes may preferably be patterned using lithographic techniques to ensure that smooth lines are patterned and finely spaced onto the substrates 41, 47.

It is preferable that the thickness of the electrodes are maintained at less than 1 µm, more preferably less than 500 nm, so that the influence of the mechanical properties of electrodes on the performance of the sensor element 40, 40', 40'', 40''', $40^{IV}$, $40^{V}$, $40^{VI}$, $40^{VII}$ is minimized.

Alternatively, if the electrodes are being placed onto a substrate that does not flex significantly, a thin film type ink can be used to provide the electrode. Such films can be patterned using printing techniques such as inkjet, pad, and offset printing, among others.

Nanoparticulate conducting inks can be employed for this layer. In order to improve the mechanical robustness of the ink, it may be sintered after deposition. Low temperature sintering of the nano-ink is only suitable when depositing conductors onto films with high temperature resistance, such as fluorene polyarylates, polycarbonate, polyethersulfone, polyimide or heat stabilized biaxially oriented films of PET or PEN.

Another suitable alternative, which is known per se, may be to apply an LbL self assembled wear resistant layer to the electrodes.

The spacer 45 should be selected so as to present low creep and good bonds to the substrates 41, 47. For example, it can be a biaxially oriented film, that is to be laminated together with the adjacent substrates. Such lamination should be performed using the thinnest possible adhesive layers (preferably thermosetting adhesives), as the presence of adhesive may adversely affect creep. Many films are commercially available with suitable adhesive surface layers.

The spacer 45 can also be provided in the form of a patterned printed layer of a curable epoxy resin, a high performance polyurethane resin or alternative, that may be further cured and used both as the spacer 45 and to bond together adjacent substrates 41, 47. In this case, care must be given to creeping of the spacer 45 during use, and reinforced resin systems may be used for the spacer 45 to further improve its mechanical properties.

The spacer may include both an extension of the cavity 48 within the sensor (air reservoir) as well as a vent 46 or series of vents to equalize pressures between the sensory element and the ambient environment.

External connections to the sensor element 40 may be provided in the form of printed silver traces or the like. Alternatively, it may be advantageous to use the electrode patterning technique everywhere, i.e., both for the electrodes and for the external connections. The trace thickness away from the sensing area may be increased by masking the sensor regions, and using an electrochemical technique to add conductor thickness to the traces leading from the sensor elements to the electronics.

Reel-to-reel techniques are suitable for mass production of the sensor element 40, 40', 40'', 40''', $40^{IV}$, $40^{V}$, $40^{VI}$, $40^{VII}$.

An isolation material 49a, 49b may be provided in the form of, e.g., a foamed polymer, which may generally be very soft, with small pores. The isolation material 49a, 49b should be significantly softer than the substrate materials 41, 47, so as not to interfere with the function of the sensor element 40, 40', 40'', 40''', $40^{IV}$, $40^{V}$, $40^{VI}$, $40^{VII}$, but so as to also provide a thin, but smooth interface with the surrounding surfaces.

Figure 18:
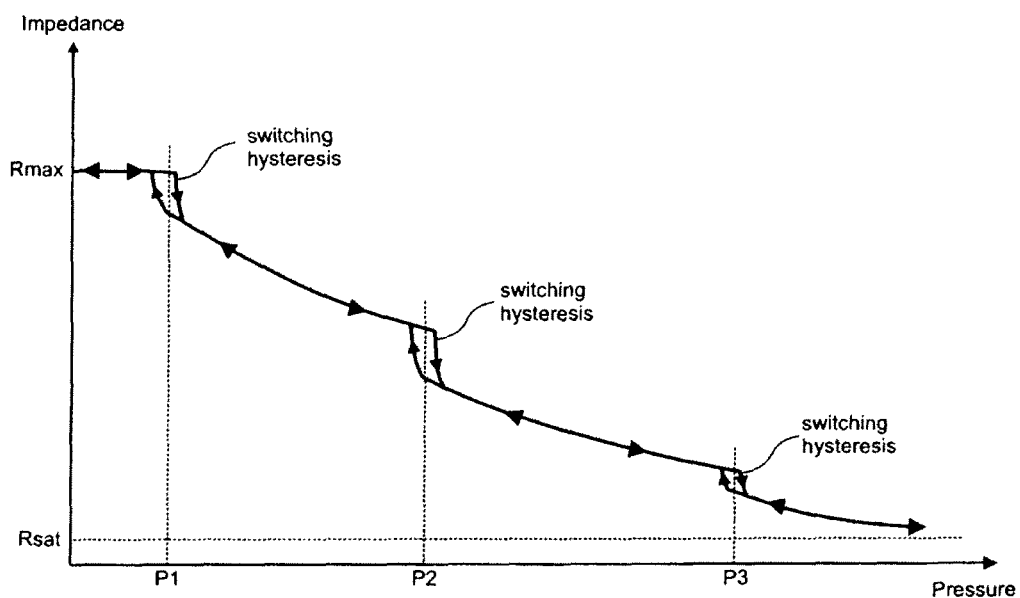

FIG. 18 illustrates the behavior of an embodiment wherein the electrodes 42a-1, 42a-2, 42a-3, 42a-4, 42a-5, 42a-6, 42b have been made from a poorly conducting material, i.e. resistive material. Such resistive materials may be provided from, e.g., nickel-chrome, tantalum, tantalum-nitride, chromium, titanium, silicon-chromium, cermet, carbon. Such materials can be deposited by evaporation, sputtering, cvd, etc.

By using such materials for the electrodes, it is possible to create sheet resistance on the electrodes 42a-1, 42a-2, 42a-3, 42a-4, 42a-5, 42a-6, 42b in a range similar to that of the resistive element 44.

In addition, thin film inks can also be used, as they are sufficiently thin so as to not adversely affect the mechanical properties of the flexible substrate 41, 47 materials. Generally, silver loaded inks are satisfactory for this purpose. Other inks based on particles of the above materials can also be used to achieve particular sheet resistance or improve mechanical strength of the contact interface between membranes. The equivalent sheet resistance of the electrode 42b can also be adjusted by patterning of the deposited electrode materials.

Furthermore, the sheet resistance can be modified by using nanoparticulate layered thin films as producible using LbL-CSA, or LbL-SA.

Figure 19A:
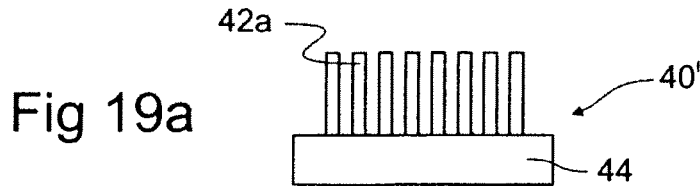
FIGS. 19a-19c illustrate alternative embodiments of the sensor element of FIGS. 11-16.
Figure 19B:
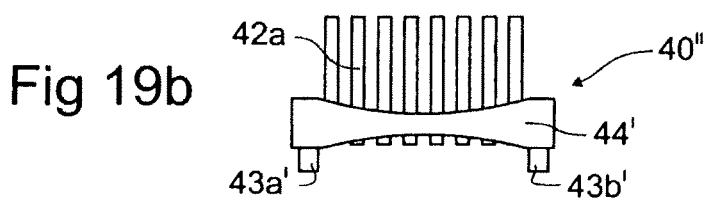
Figure 19C:
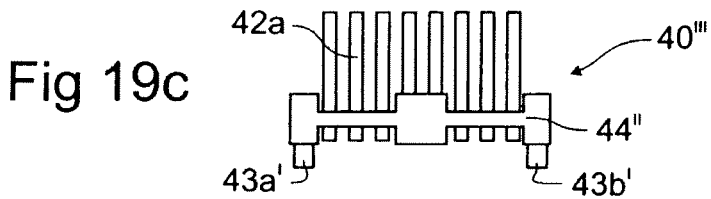

FIGS. 19a-19c illustrate alternative embodiments of the resistive element 44 and the connectors 43a, 43b. Such embodiments are useful for tailoring the pressure impedance response of the sensor element 40, 40', 40'', 40''', $40^{IV}$, $40^{V}$, $40^{VI}$, $40^{VII}$.

Specifically, they are useful for controlling the height of the various discontinuities shown in FIGS. 17 and 18.

In FIG. 19a, the resistive element 44 is formed as a substantially rectangular elongate structure, while the connectors 43a', 43b' are arranged at respective ends of the resistive element.

In FIG. 19b, the resistive element 44' presents a varying width and/or thickness, being elongate and concave, while the connectors 43a', 43b' are arranged at respective ends of the resistive element. More generally the resistive element 44' is shaped in a continuous fashion without discontinuities in width along the conducting path.

In FIG. 19c, the resistive element 44'' presents a varying width and/or thickness, including broader end portions and a broader middle portion, spaced apart by respective narrower intermediate portions. More generally, the width of the resistive element 44'' may be varied along the conductive path in a step wise fashion to tailor the step height of discontinuities in the pressure-impedance response of the sensor element 40'''. This form of adjustment of the resistive element 44'' is a simple way of tailoring the sensor response to distinguish critical pressure transitions when used in hostile environments with significant EMI.

Figure 20A:
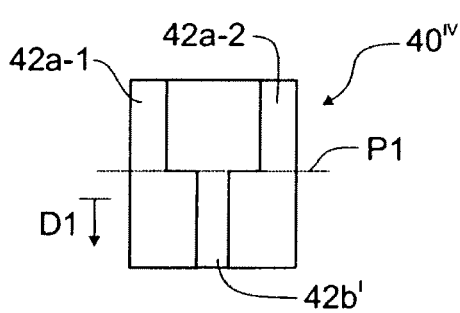
FIGS. 20-22 illustrates yet further embodiments of the sensor element of FIGS. 11-16.
Figure 20B:
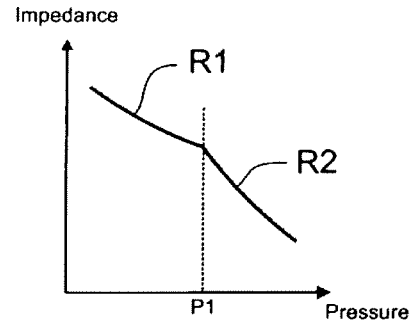

FIGS. 20a and 20b illustrates an embodiment of an electrode configuration, wherein the increase in contact area between the first electrode 42a-1, 42a-2 and the second electrode 42b' alters the slope of the pressure impedance relationship of the sensor element 40$^{IV}$ around the point P1. Such an embodiment may be provided by using poorly conducting electrodes. The effect may be achieved by the first electrode elements 42a-1, 42a-2 being of a varying width and/or a reduction in gap spacing between two elements at some point along their length. This may be useful for enhancing the sensitivity of the sensor to pressure in a particular range. This can be especially useful for adjusting the sensitivity of the sensor element 40, 40', 40'', 40''', 40$^{IV}$, 40$^{V}$, 40$^{VI}$, 40$^{VII}$ at higher pressure levels where it is very important to remain below a maximum pressure limit while performing a therapy.

FIG. 20b illustrates the behavior such an embodiment: the slope of the pressure-impedance curve is discontinuous at the point P1.

Figure 21A:
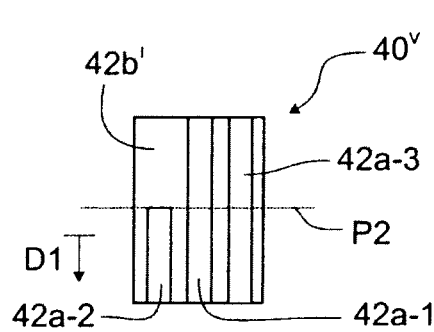
Figure 21B:
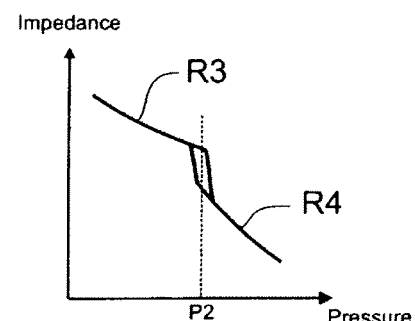

FIGS. 21a-21b illustrates another embodiment of an electrode configuration, wherein the increase in contact area between the first electrode element 42a-1, 42a-2, 42a-3 and the second electrode 42b'' alters the slope of the pressure-impedance relationship of the sensor element 40$^{V}$ around point P2 while also introducing a discontinuity around P2. In this embodiment, the lengths of the elements 42a-1, 42a-2, 42a-3 do not extend across the entire sensor area. Then, as the contact region between the first and second electrodes 42a, 42b expands with increasing applied pressure, more or less elements will come into contact.

This will cause both a change in sensitivity similar to the example of FIGS. 20a-20b, but will also produce a jump discontinuity at the point P2 of contact with the shorter element. This point can then be more easily used as a pressure calibration point for the sensory array.

Figure 22A:
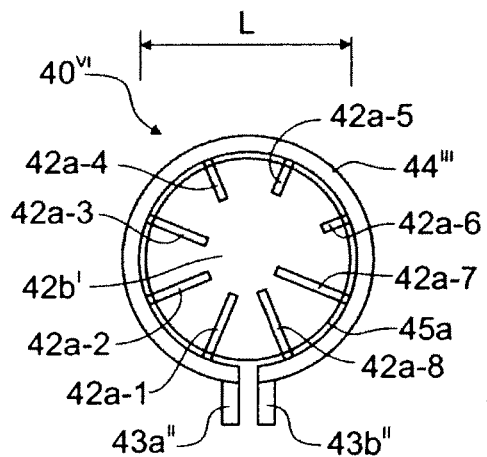

FIG. 22a illustrates another embodiment of a sensor element 40$^{VI}$, wherein the resistive element 44''', providing the conductive path, is substantially circular, and the "fingers" of the first electrode 42a-1, 42a-2, 42a-3, 42a-4, 42a-5, 42a-6, 42a-7, 42a-8 extend substantially radially from the resistive element and towards the center of the sensor element 40$^{VI}$.

Connectors 43a'' and 43b'' are arranged at the respective ends of the resistive element 44'''. The elements of the first electrode 42a-1, 42a-2, 42a-3, 42a-4, 42a-5, 42a-6, 42a-7, 42a-8 may present different lengths, and the spacer 45a may be provided as a ring around the sensor element 40$^{VII}$. The second electrode 42b' is spaced from the first electrode element 42a-1, 42a-2, 42a-3, 42a-4, 42a-5, 42a-6, 42a-7, 42a-8 in a manner similar to that described with respect to FIGS. 11-16.

Sensor element 40$^{VI}$ is advantageous in that its circular form allows for uniform stress at the spacer 45a, thereby providing a sensor element 40$^{VI}$ with improved fatigue life.

Figure 22B:
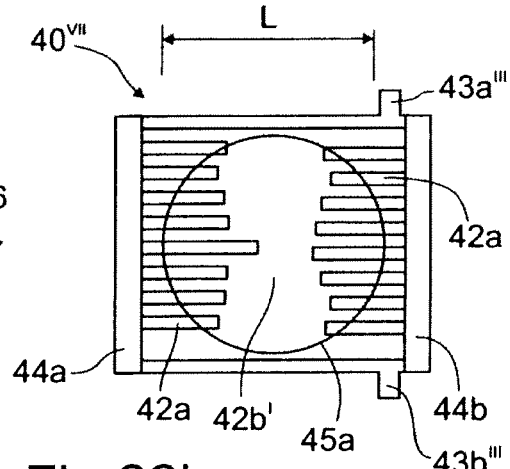

FIG. 22b illustrates another embodiment of a sensor element 40$^{VII}$, comprising a pair of resistive elements 44a, 44b, each forming a respective conduction path. The resistive elements 44a, 44b have respective connectors 43a''', 43b''', which may also interconnect the resistive elements 44a, 44b, as illustrated, such that they are connected in parallel. A number of first electrode elements 42a are connected to the first resistive element 44a at a respective position along the conduction path of the first resistive element 44a. Similarly, a number of first electrode elements 42a are connected to the second resistive element 44b at a respective position along the conduction path of the second resistive element 44b. Thus, first electrode elements 42a extend from the respective resistive element 44a, 44b and into an active area of the sensor, which may generally coincide with the cavity of the sensor element 40$^{VII}$. The cavity is defined by the patterned shape of the spacer 45a. In this example, the cavity is defined by a spacer 45a comprising a circular hole as shown in FIG. 22b.

Extra ventilation and air reservoirs are not shown in FIG. 22b but may be added as previously discussed.

The first electrode elements of this embodiment may, but do not need to, present mutually different lengths. This embodiment increases the maximum possible switch levels available from the sensor without significantly increasing the size of the sensor. It also adds flexibility in terms of optimizing the pressure-impedance response of the sensor element.

In FIGS. 11-13, 16 and 22a-22b, the characteristic length L, characteristic width W and overall sensor thickness T (including isolating layers 49a, 49b) are indicated. Also, in FIG. 16, there is indicated the sensor body thickness S.

Generally, the sensor body thickness R should be very small, preferably less than 50 pm, more preferably less than 25 μm or less than 20 μm. The overall sensor thickness T is preferably less than 1.5 mm, more preferably less than 1 mm, more preferably less than 0.5 mm or 0.2 mm. The ratio between L and/or W and T may be about 1.

Referring to FIGS. 4-10, the same ratios between sensory region length/width and thickness, and between sensor body thickness and isolation layer thickness, apply.

It is not a requirement that the electrode elements be arranged as lines in an array (as shown in FIGS. 11-14, 19a-19c, or 22b), or as radial spokes (as shown in FIG. 22a). It is quite possible to attain useful sensors by providing sensor elements comprising first electrode elements with rectangular, linear, elliptical, circular, spiral, or exotic shapes and perturbations thereof.

It is also possible to mix and match differently shaped electrode elements and cavities to suit the particular needs of a given application.

One example that can be particularly useful is a combination of rectangular-shaped electrode elements in a grid-like formation (easily patterned) with a circular-shaped cavity (minimized edge stress). Such a circular-shaped cavity can be easily provided by a perforated film spacer 45. An example of this configuration is exemplified by FIG. 22b.

The description will now focus on schemes for connecting and arranging the above discussed sensor elements. In particular, these schemes address the problem of variations in pressure within the measuring device. Contact pressures between surfaces can vary widely, and often in a periodic manner, over short distances between two surfaces in contact. Such variations occur due to the random nature of contact mechanics and the texture of the materials at the contact interface. These variations are further exaggerated when light pressures are applied between textured surfaces (such as fabric layers pressed against a body for example). In these cases, pressure is primarily transmitted through apexes at the interface between the surfaces during initial contact and tends to settle out as the interface materials creep under continued contact pressure.

If a sensor system is to adequately measure the contact pressures between two surfaces, it should preferably be able to cope with these unavoidable aspects of contact mechanics.

The geometric issues of measuring representative stresses between two surfaces can be remedied by using sufficiently thick isolation layers between the sensor elements and the surfaces in question to alleviate pressure variations in the vicinity of the pressure sensor. This task is not easy to accomplish when measuring pressures applied to body parts as overly thick isolation layers make the device uncomfortable for the patient, and curvature makes use of such layers impractical. Instead, the sensor elements should be made sufficiently small such that a thin isolation layer is suitable for averaging out the microscopic stress variations present in the immediate vicinity of a single sensor element. Unfortunately, the randomness of contact mechanics prevents a lone sensor from recovering the overall characteristics of stress between the contact surfaces.

One way of handling this problem is to provide a large number of miniature sensors, and to analyze the signals from each of the sensors in order to provide a useful result, which may be an average pressure estimate over the area of the sensor array. However, this would require a large number of sensors to be individually connected to a processing unit. The processing unit would also need sufficient processing power to perform the analysis from such a large number of sensors, and under realistic operating conditions with associated cost, power, and time constraints.

This task is further complicated in that pressure sensor elements are nonlinear by nature. Therefore, the processing unit would require an array of individually calibrated lookup-tables, or configurable algorithms to convert sensor singles into "pressure estimates", and further analyze the results mathematically under real-time conditions. As sensor elements will also age during use, a means of updating the lookup-tables in the processing unit would be required.

Instead, the present disclosure provides connectivity schemes to naturally recover useful pressure related information directly from groupings of pressure sensor elements, regardless of sensor nonlinearities and in a real-time fashion, without the need for large numbers of routed traces or hefty computational requirements.

Such pressure related information includes (but is not limited to) the average pressure, the pressure gradient vector, the magnitude of the pressure gradient, and higher order spatial derivatives of the pressure applied to the cluster or portion of the cluster.

Figure 23A:
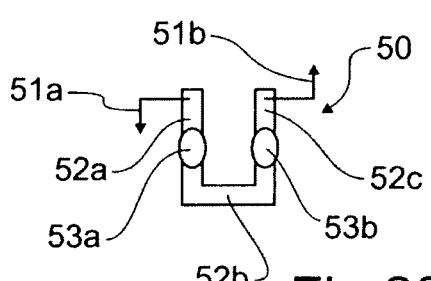
FIGS. 23a-23b illustrate generic connection schemes for a pair of sensor elements.
Figure 23B:
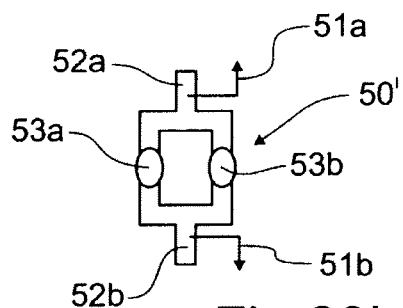

For clarity, FIGS. 23a and 23b illustrate generic connection schemes for a pair of two port sensor elements. A two port sensor element is simply a sensor element with only two electrodes. FIG. 8 shows a sensor element 30' with more than two electrodes.

FIG. 23a illustrates a pair 50 of sensor elements 53a, 53b, which via first and second conductors 52a, 52c are connectable to an external circuit and which via a third conductor 52b are interconnected in a serial manner. External connections are provided at 51a and 51b.

FIG. 23b illustrates a pair 50' of sensor elements 53a, 53b, which via first and second conductors 52a, 52d are connectable to an external circuit and which are interconnected in a parallel manner. External connections are provided at 51a and 51b.

The solution of the problem of recovering pressure related information over an area of the surface is to provide a cluster 50'', 50''', $50^{IV}$, $50^V$, $50^{VI}$ of sensor elements, which are interconnected in such a manner as to provide a minimum of external connections, ideally only two, whereby an impedance value is provided between these two external connections that is representative of the desired pressure related information. The cluster should contain at least one sensor element which is connected in series with one or more other sensor elements, and at least one sensor element which is connected in parallel with one or more further sensor elements.

Figure 24:
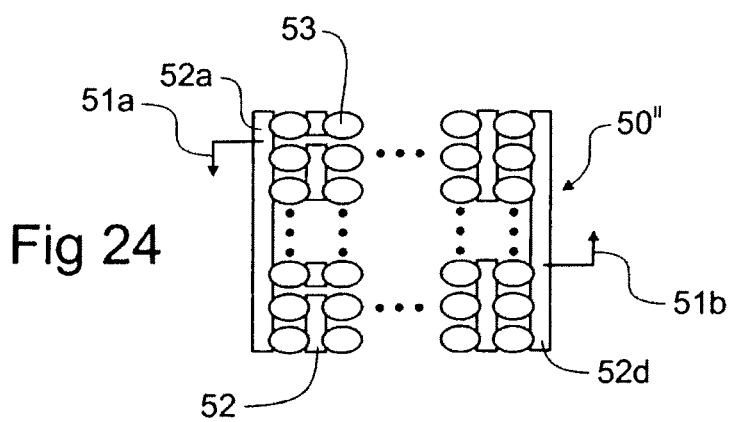
FIGS. 24-26 illustrate connection schemes for a plurality of sensor elements.

FIG. 24 schematically illustrates an example of a cluster 50'' of sensor elements. The cluster is provided as an n×m array of sensor elements 53, with a first electrode 52a providing a first external connection 51a, a final electrode 52d providing a second external connection 51b, and a plurality of m columns of sensor elements 53, each column consisting of n sensor elements 53 connected along the conduction path between the first electrode 52a and a final electrode 52d by a plurality of generally placed internal electrodes 52. The internal electrodes of the cluster are generally arranged to connect small groups of sensor elements 53 in adjacent columns to each other. Hence, the internal electrodes 52 may extend vertically in FIG. 24 so as to contact two or more of the sensor elements 53. The connections are established such that the required pressure related information can be obtained from the external connections 51a, 51b. For a cluster with only two external connections, this pressure related information is most commonly the representative of the average pressure applied to the cluster.

To achieve a representation of the average pressure applied to the cluster, the connections within the cluster should preferably contain at least one polygon network element. The details are described below in more detail with examples.

The sensor elements included in the cluster need not have the same properties, nor must they connect only two electrodes. It is also not necessary that every position in the cluster be populated with either sensor element or an electrode element (e.g., clusters may contain regions free from sensor elements or electrodes).

Figure 25:
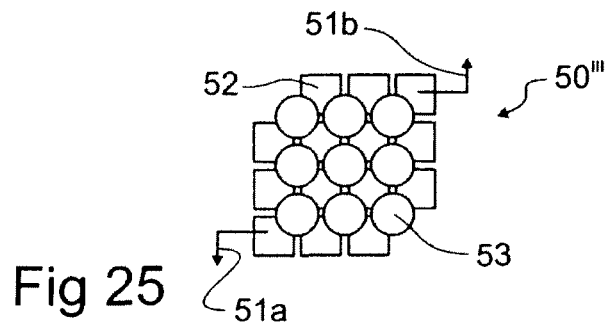

FIG. 25 illustrates another embodiment of a cluster 50''' wherein the sensor elements 53 are in contact with three or four different electrodes 52, thus providing a more complex connectivity. Sensor elements with more than two electrodes are capable of resolving pressure gradients internally and thus produce a higher effective resolution than sensor elements with only two electrodes. Such sensor elements can also have reduced susceptibility to temperature and humidity fluctuations when properly connected into clusters.

Figure 26:
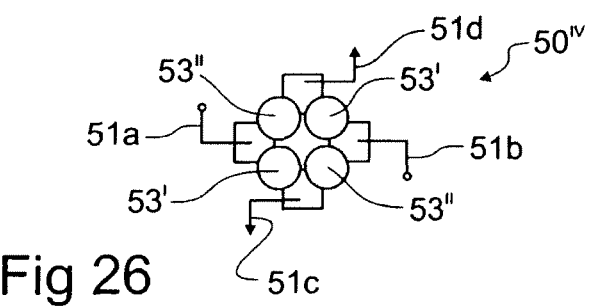

FIG. 26 illustrates yet another embodiment of a cluster $50^{IV}$, wherein four sensor elements 53', 53'' each contact two electrodes, and wherein external connectors are provided at 51a, 51b, 51c, 51d. A cluster with more than two external connections is capable of resolving higher order pressure related information from the cluster, such as the pressure gradient magnitude and direction, and higher order spatial derivatives of the pressure over the cluster. Such arrangements also provide natural compensation for changes in the sensor properties due to aging and temperature-humidity fluctuations.

The embodiment demonstrated by the cluster $50^{IV}$ is particularly useful when sensor elements 53' and sensor elements 53'' are provided with different pressure sensitivities. In this case, if a voltage is applied across external connectors 51c, 51d, then the differential voltage between electrodes 51a, 51b will be representative of the average pressure applied to the cluster $50^{IV}$.

Figure 27:
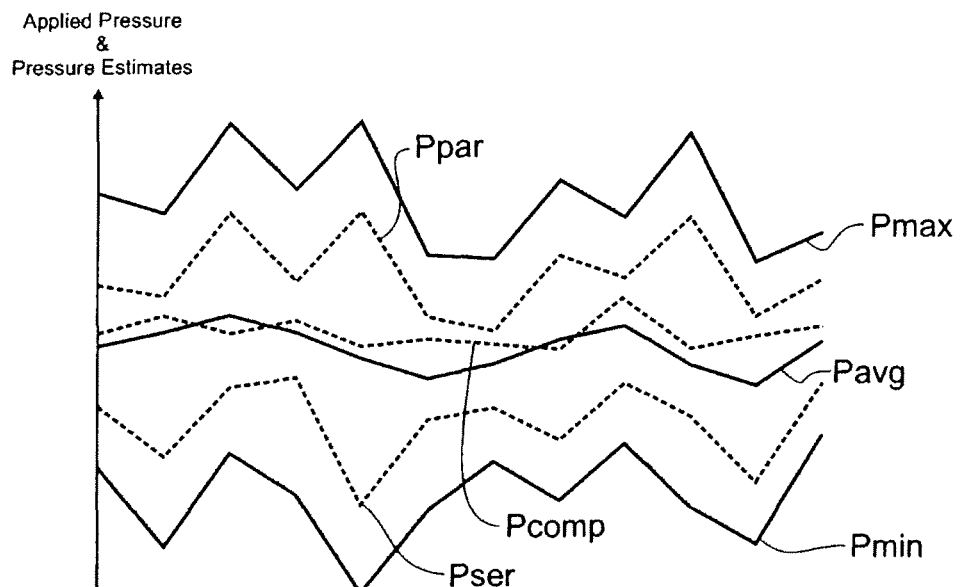
FIG. 27 is a diagram illustrating the behavior of the connection schemes of FIGS. 24-26.

FIG. 27 schematically illustrates a signal $P_{par}$ from a sensor cluster comprising only parallel connected sensor elements, a signal $P_{ser}$ from a sensor cluster comprising only serial connected sensor elements and a composite signal $P_{comp}$ from a cluster comprising both serial and parallel connected sensor elements, in a situation with a maximum measured pressure $P_{max}$, a minimum measured pressure $P_{min}$ and a actual average pressure $P_{avg}$ over the entire area. It is demonstrated that an optimally connected cluster will give rise to pressure estimates $P_{comp}$ which have values centered around those of the average applied pressure $P_{avg}$ with a variance that is much smaller than that of the overall applied pressure. General connections depicted by $P_{ser}$ and $P_{par}$ fail to attain a similar correlation.

Figure 28:
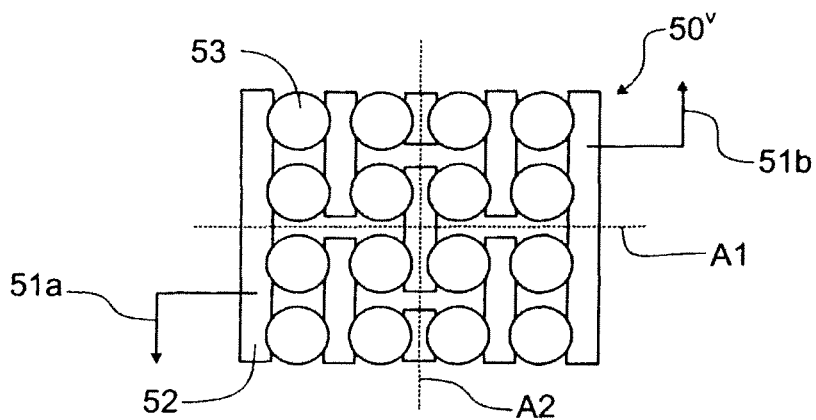
FIGS. 28-33 illustrate further connection schemes equivalent circuits.

FIG. 28 illustrates another embodiment of a cluster $50^V$, comprising both serial and parallel connected sensor elements. This embodiment is a specific example of a 4×4 cluster. This example cluster $50^V$ comprises first and second axes of symmetry A1, A2. The cluster also comprises a quadrilateral polygon network of sensory elements. This polygon connection is clarified in more detail by FIGS. 29-30.

Figure 29:
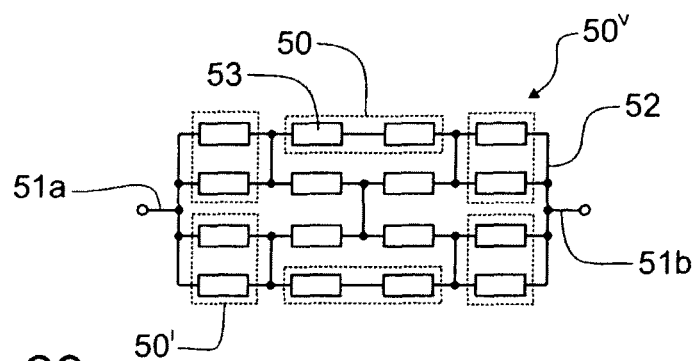

FIG. 29 illustrates an equivalent circuit diagram of the embodiment of FIG. 28, illustrating, by the dotted boxes, the serial connected pairs 50 of sensor elements and the parallel connected pairs 50' of sensor elements.

Figure 30:
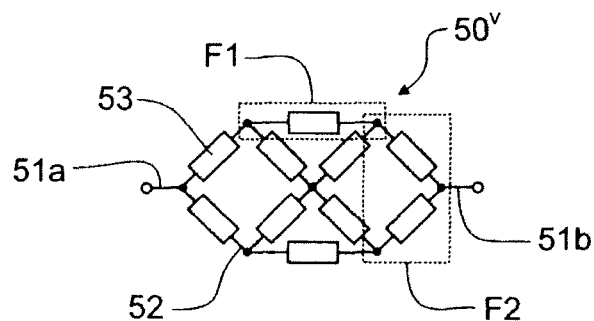

FIG. 30 illustrates a reduced equivalent circuit diagram of the embodiment of FIG. 28. The reduced equivalent circuit diagram is achieved by merging all (purely) serial and parallel connected pairs into equivalent circuit elements. Such a process is continued until there are no remaining purely serial or parallel connected pairs to further reduce. The reduced equivalent circuit clearly demonstrates that the cluster $50^V$ is electrically equivalent to a polygon network element as described in March RH, Polygons of resistors and convergent series, American Journal of Physics, 61(10), 1993, pg. 900. Faces F1 and faces with internal connections F2 are illustrated. In this case, the cluster $50^V$ comprises a single quadrilateral polygon network element wherein two faces F1 have one impedance element while the other two faces are faces with internal connections F2, or "tapped faces".

The impedance of the cluster $50^V$ as measured between the external connections 51a, 51b is representative of the average pressure applied to the cluster $50^V$.

Figure 31:
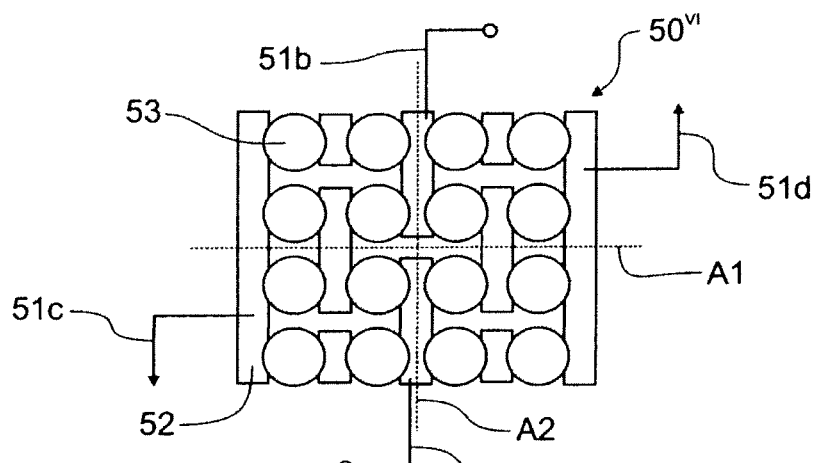

FIG. 31 illustrates a further embodiment of a cluster $50^{VI}$, comprising both serial and parallel connected sensor elements. This embodiment is another specific example of a 4×4 cluster. This embodiment comprises a first set of external connections 51c, 51d and also a second set of external connections 51a, 51b, which may be used to garner further information about pressure distribution inside the cluster. For example, such a second set of external connections may be used to determine if the pressure is lower or higher in any quadrant of the cluster, i.e., it can obtain 1st order information regarding the macroscopic derivative of the pressure distribution applied to the sensor cluster. The cluster $50^{VI}$ is electrically equivalent to a connection of two triangular polygon network elements with a shared face F3. This equivalence is further clarified by FIGS. 32-33.

Figure 32:
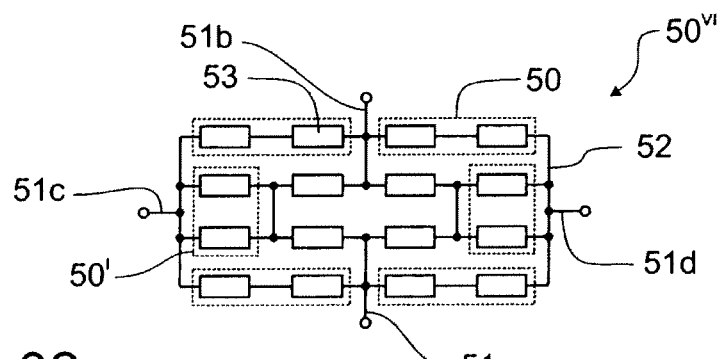

FIG. 32 illustrates an equivalent circuit diagram of the embodiment of FIG. 31, illustrating the serial connected pairs 50 of sensor elements and the parallel connected pairs 50' of sensor elements.

Figure 33:
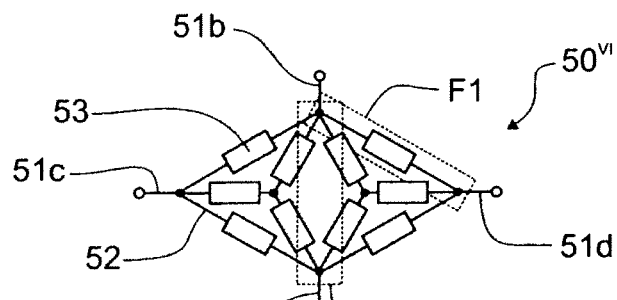

FIG. 33 illustrates a reduced equivalent circuit diagram of the embodiment of FIG. 31. The equivalent circuit demonstrates that equivalent circuit for the 20 cluster $50^{VI}$ comprises a group of polygon network elements. Faces F1 and shared face F3 are illustrated. In this case, cluster $50^{VI}$ comprises a connection of two triangular polygon network elements with a shared face wherein Faces F1 have a single impedance element while shared face F3 is missing an impedance element.

The impedance of the cluster $50^{VI}$ as measured between the first set of external connections 51c, 51d is representative of the average pressure applied to the cluster $50^{VI}$ Alternatively, if a voltage is applied across the first set of external connections 51c, 51d, then the voltages and voltage difference measured between the second set of external connections is representative of the pressure gradient applied to the cluster $50^{VI}$.

In the above described clusters, the overall impedance of the cluster can be further tailored to achieve values that are most suitable for the external electronics. To achieve this end, the optimum connectivity is a combination of serial and parallel connections with weight to more serial or more parallel depending on the desired overall impedance of the cluster.

As FIGS. 23-33 depict connections in a schematic fashion, it is to be understood that connectivity plays no bearing on the actual geometric layout of the cluster. It is not a requirement that the clusters be formed in rectangular arrays of sensor elements. Furthermore, it is possible that the sensor elements be printed on two sides of a substrate with connectivity between them forming a single cluster.

It is also understood that connectivity of sensor elements scattered over a wide area can be equivalent to the connectivity of sensor element in a tight packed arrangement, and that a sensor elements arranged in a grid can have equal connectivity to sensor elements arranged randomly over an area.

It is not a requirement that sensor elements be connected only to adjacent electrodes. Higher order connectivity, achievable by multi-layered connections, is advantageous for some applications such as measurement of temporal pressure events with related spatial heterogeneity throughout the cluster (e.g., pressure waves).

It is further understood that many physical connectivities within a cluster can lead to the same representative reduced equivalent circuit. As an example, the reduced equivalent circuit of FIG. 33 could represent a cluster of ten sensor elements 53 connected precisely as shown in FIG. 33.

It is further understood that each sensor element 53 within the clusters could equally represent a nested cluster. As an example, the sensor element 53' as shown in FIG. 26 may actually represent a cluster with two external connections such cluster $50^{VI}$ while sensor element 53" as shown in FIG. 26 may represent a different cluster with two external connections such as cluster $50^V$.

The sensor clustering principle, as exemplified with reference to FIGS. 24-33 is mainly useful for analog sensors, such as those described with reference to FIGS. 4-10.

In one embodiment, a sensor system may contain a cluster of a plurality sensor elements of the type described with reference to FIGS. 4-10, and one or more sensors of the type described with reference to anyone of FIGS. 11-22.

A cluster 70 comprising a plurality of sensor elements 40 as described with reference to FIGS. 11-22, can be arranged such that the pressure-impedance behavior of the cluster 70, as measured between the external connections 51a, 51b, is demonstrated by FIG. 17. Similar behavior can be obtained from clusters comprise different sensor elements as demonstrated in the following two examples.

In the first example, a cluster 70 consists of five sensor elements 40 as described with reference to FIGS. 11-22, each having only two first electrodes 42a, which are connected together serially. The size of the cavity 48, positioning of the first electrode elements 42a with respect to the cavity 48, and/or spacing S between the first electrode elements 42a are individually adjusted for each sensor such that the sensor element provides a corresponding switching pressure P1, P2, P3, P4 or P5.

In the second example, a cluster 70 comprising two sensor elements 40 as described with reference to FIGS. 11-22, one sensor element having three first electrode elements 42a, and a second sensor element having four first electrode elements 42a, wherein the sensor elements 40 are connected serially and the size of the cavity 48, positioning of the first electrode elements 42a with respect to the cavity 48, and/or spacing S between the first electrode elements 42a, are individually adjusted for each sensor element such that the first sensor element provides switching pressures P1 and P2, and the second sensor element provides switching pressures P3, P4 and P5.

In another embodiment, a sensor system may contain a first cluster of a plurality sensor elements of the type described with reference to FIGS. 4-10, and a second cluster of sensors of the type described with reference to anyone of FIGS. 11-22.

In particular, the second cluster may comprise sensors having resistive electrodes, e.g., as discussed with reference to FIG. 18.

The sensor clusters and/or systems may be enclosed within a common enclosure, such as the one designated by reference numerals 26, 34, 49a or 49b.

Individual sensor elements, sensor clusters or sensor systems may be connected to a measuring device for measuring pressure.

Referring to FIGS. 34-36, the sensor elements, sensor clusters or sensor systems may be used for measuring pressure on a body part 60, which in FIGS. 34-36 is illustrated by a lower leg. A plurality of sensor devices 62, 62', 62", each being in the form of a sensor element, sensor cluster or sensor system, may be distributed over a carrier 61, 61', which may be in the form of a flexible sheet, in order to conform to the body part on which measurements are to be made.

The sensor devices 62 may be connected via conductor devices 66 (cables, wires, conducting traces, etc.) to a central point 63, wherein connectors for connection to external equipment may be provided, or wherein the electronics itself may be provided. The carrier 61, 61' may thus be the substrate (c.f. reference numerals 21, 31, 41, 47) on which the sensor element is arranged. The sensor devices 62 may be distributed over an area of the carrier 61, such as is illustrated in FIG. 34. Alternatively, or as a complement, sensor devices 62' or substantially along a line, such as is illustrated in FIG. 35.

Alternatively, the sensor devices 62" may be distributed over the entire carrier 61', with interconnection buses 65a, 65b, 65c provided, e.g., at the edges (65a, 65c) of the carrier 61, and/or along the length of the carrier 61 (65b).

The carrier may be in the form of a flexible sheet of garment or film, which optionally may be breathable. The carrier 61 may form the substrate as illustrated in FIGS. 4-22. In order to form a measuring device for measuring pressure on a body part, the carrier 61 with the sensors may be part of a laminated structure, which may contain one or more pressure smoothing layers, arranged on one or both sides of the carrier 61. The smoothing layers may be intimately laminated or printed onto either side of the carrier 61, such that the stresses at the interface between the sensor element and its surroundings can be sufficiently smoothed before they reach the surface of the sensing element.

Such smoothing layer may be in the form of a microcellular foam structure. In other embodiments, it may be a printed layer of rubber, a laminated non-woven fabric etc.

The mechanical properties and thickness ratios between the smoothing layer and transverse sensor moduli and dimensions may be selected so as to ensure that pressure is effectively smoothed upon reaching the sensor element surface. The total sensor and smoothing layer thickness should preferably be less than 1.5 mm, more preferably less than 1.0 mm, even more preferably less than, 0.5 mm and most preferably less than 0.2 mm, and therefore the sensor element should be extremely thin to accommodate a sufficiently thick smoothing layer into the small amount of space provided. The smoothing layer may be chosen such that it is preferably 5-10 times the thickness of the sensor element.

In order for the smoothing layer to be effective, it is also preferable that the length, width or diameter of the sensing area of the sensor element be roughly of the same order of magnitude as the thickness of the total sensor and smoothing layer thickness.

The carrier 61 may be included in a device for compression treatment of the body part. Hence, the device may comprise further layers 200 (FIG. 37) housing actuators etc., for providing the compression movement.

As one example, the layer 200 may form part of an inflatable bladder, which is used to provide a pressure to a body part in a per se known manner.

In yet another embodiment, the substrate 21, 31, 41, 61, 61', upon which the sensor element is arranged, may be a wall of such a bladder, i.e., the substrate may be integrated with the wall of the bladder.

In other embodiments, the compression device may, as non-limiting examples, be of the type described in any one, or a combination of, US 2004/0073146A1, US 2002/0173735A1, EP 1 324 403 A1, U.S. Pat. No. 5,997,465, WO 2004/093763 A1, US 2005/0043657 A1, U.S. Pat. No. 6,123, 681, U.S. Pat. No. 6,494,852 B1, U.S. Pat. No. 6,198,204 B1 or US 2004/0167375 A1.

Figure 37:
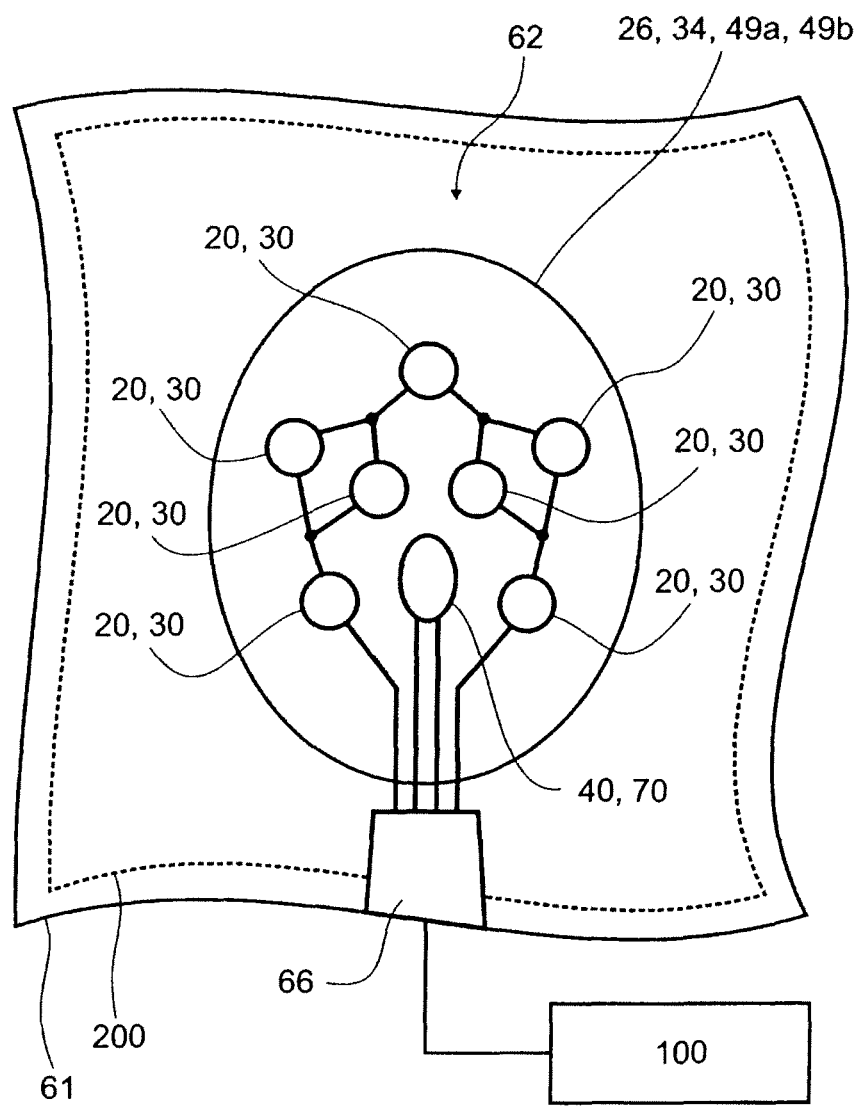
FIG. 37 schematically illustrates a sensor cluster forming part of a sensor system.

Referring to FIG. 37, there is illustrated a detail of a carrier 61, upon which a sensor device 62 is provided, and connected via a conductor device 66 to a measuring device 100. The sensor device comprises at least one, preferably more, pressure sensor element 20, 30 of the first type as described with reference to FIGS. 4-10, or clusters $50''$, $50'''$, $50^{IV}$, $50^{V}$, $50^{VI}$ of such pressure sensor elements, and at least one pressure sensor element 40 of the second type, or cluster 70 thereof, as described with reference to FIGS. 11-22.

In one embodiment, the sensor device 62 may comprise a plurality of sensor elements of the first type, which are arranged as a sensor cluster $50''$, $50'''$, $50^{IV}$, $50^{V}$, $50^{VI}$, as described with reference to FIGS. 24-33, and optionally one or more sensor elements of the second type.

In another embodiment, the sensor device 62 may also comprise a plurality of sensor elements of the second type, which are arranged as a sensor cluster as described with reference to FIGS. 24-33.

The sensor elements may be arranged within a common encapsulation 26, 34, 49a, 49b.

As indicated, the sensors and sensor systems described herein may be used for measuring contact pressure between a body part and a compression device, between two body parts, between a body part and some external device, such as a steering wheel (e.g., when arranged in/on a glove or in/on the steering wheel), a surgical tool, a floor (e.g., when arranged in/on a shoe).

The invention claimed is:

1. A pressure sensor element comprising:
    a non-conducting elastomeric portion; and
    a plurality of particles having a size in the range of 0.1 to 250 µm comprising a non-conducting elastomeric body having an electrically conducting surface, said particles being arranged as at least one conducting particle layer on said non-conducting elastomeric portion, said non-conducting elastomeric body of the particles governing the mechanical properties of the particles, said electrically conducting surface of the particles governing the electrical properties of the particles, and further, when said pressure sensor element is subjected to pressure, the relative positions of the particles arranged as the at least one conducting particle layer change, thereby changing the impedance of the pressure sensor element, wherein the pressure sensor element further comprises:
a first electrode electrically connected to a first portion of the at least one conducting particle layer, and
a second electrode electrically connected to a second portion of the at least one conducting particle layer.

2. The pressure sensor element of claim 1, wherein a second non-conducting elastomeric portion is arranged relative to the at least one conducting particle layer such that the at least one conducting particle layer is enclosed by the non-conducting elastomeric portion and the second non-conducting elastomeric portion.

3. A sensor cluster comprising at least three pressure sensor elements, each pressure sensor element as claimed in claim 1, wherein the sensor cluster comprises:
at least one pressure sensor element or group of pressure sensor elements, which is connected in parallel with another pressure sensor element, or group of pressure sensor elements, and
at least one pressure sensor element or group of pressure sensor elements, which is connected in series with another pressure sensor element, or group of pressure sensor elements.

4. The sensor cluster of claim 3, wherein the sensor cluster comprises pressure sensor elements forming a circuit, a reduced equivalent circuit of which substantially comprises a polygon network element.

5. A sensor system, comprising:
at least one first pressure sensor element comprising:
a non-conducting elastomeric portion,
a plurality of particles having a size in the range of 0.1 to 250 μm comprising a non-conducting elastomeric body having an electrically conducting surface, said particles being arranged as at least one conducting particle layer on said non-conducting elastomeric portion, and further, when said at least one first pressure sensor element is subjected to pressure, the relative positions of the particles arranged as the at least one conducting particle layer change, thereby changing the impedance of the sensor element,
a first electrode electrically connected to a first portion of the at least one conducting particle layer, and
a second electrode electrically connected to a second portion of the at least one conducting particle layer; and
at least one second pressure sensor element comprising:
a resistive element providing a conduction path,
a first electrode, and
a second electrode which, in a quiescent state, is spaced from said first electrode by a non-conducting elastomeric material having one or more conducting layers, but when said pressure sensor element is subjected to a pressure, the second electrode is arranged to contact said first electrode through the one or more conducting layers or said resistive element.

6. A device for measuring contact pressure applied on a body part, comprising at least one pressure sensor element, wherein the at least one pressure sensor element comprises:
a non-conducting elastomeric portion; and
a plurality of particles having a size in the range of 0.1 to 250 μm comprising a non-conducting elastomeric body having an electrically conducting surface, said particles being arranged as at least one conducting particle layer on said non-conducting elastomeric portion, said non-conducting elastomeric body of the particles governing the mechanical properties of the particles, said electrically conducting surface of the particles governing the electrical properties of the particles, and further, when said pressure sensor element is subjected to pressure, the relative positions of the particles arranged as the at least one conducting particle layer change, thereby changing the impedance of the pressure sensor element, wherein the device further comprises a compression treatment device to provide compression treatment of said body part which incorporates the at least one pressure sensor element therein.

* * * * *